United States Patent
Fontaine et al.

(10) Patent No.: US 11,749,377 B2
(45) Date of Patent: Sep. 5, 2023

(54) METHOD AND ELECTRONIC SYSTEM FOR PREDICTING AT LEAST ONE FITNESS VALUE OF A PROTEIN, RELATED COMPUTER PROGRAM PRODUCT

(71) Applicant: PEACCEL, Saint-Denis (FR)

(72) Inventors: Nicolas Fontaine, La Réunion (FR); Frédéric Cadet, Paris (FR)

(73) Assignee: PEACCEL, Saint-Denis (FR)

( * ) Notice: Subject to any disclaimer, the term of this patent is extended or adjusted under 35 U.S.C. 154(b) by 606 days.

(21) Appl. No.: 15/565,893

(22) PCT Filed: Apr. 14, 2016

(86) PCT No.: PCT/EP2016/058287
§ 371 (c)(1),
(2) Date: Oct. 11, 2017

(87) PCT Pub. No.: WO2016/166253
PCT Pub. Date: Oct. 20, 2016

(65) Prior Publication Data
US 2018/0096099 A1 Apr. 5, 2018

(30) Foreign Application Priority Data
Apr. 14, 2015 (EP) ..................... 15305552

(51) Int. Cl.
| | | |
|---|---|---|
| G16B 30/00 | (2019.01) | |
| G16B 20/00 | (2019.01) | |
| G16B 20/50 | (2019.01) | |
| C07K 2/00 | (2006.01) | |
| G06F 17/14 | (2006.01) | |
| C12N 15/10 | (2006.01) | |
| C40B 40/10 | (2006.01) | |

(52) U.S. Cl.
CPC ............... *G16B 30/00* (2019.02); *C07K 2/00* (2013.01); *G06F 17/14* (2013.01); *G16B 20/00* (2019.02); *G16B 20/50* (2019.02); *C12N 15/1089* (2013.01); *C40B 40/10* (2013.01)

(58) Field of Classification Search
CPC .......... G06N 7/005; G06N 5/04; G06N 5/025; G16B 20/00; G16B 30/00; G16B 20/50; G16B 15/00; G16B 50/00; G16B 40/00; G16B 15/20; G16B 40/10; G01N 33/68; G01N 33/6848; G01N 33/6851; G06K 9/6201; G06F 17/14; G06F 17/142; G06F 17/18; G06F 17/17
See application file for complete search history.

(56) References Cited

U.S. PATENT DOCUMENTS

| | | |
|---|---|---|
| 2004/0029126 A1 | 2/2004 | Bloecker et al. |
| 2021/0265014 A1* | 8/2021 | Cadet ..................... G16B 30/10 |

FOREIGN PATENT DOCUMENTS

WO WO 2008/129458 10/2008

OTHER PUBLICATIONS

Nwankwo 2011 Digital Signal Processing Techniques: calculating biological functionalities. J Proteomic Bioinformatics 4(2) 260-268. (PTO-1449) (Year: 2011).*
Berland Jul. 2013, A new method for spectral characterization of protein families from sequence information using Fourier transform. JOBIM 2013. Eds Gaspin et al. Item P82, 2 pages. (PTO-1449). (Year: 2013).*
Berland et al., "A new method for spectral characterization of protein families from sequence information using Fourier Transform," Poster, *8th IAPR International Conference on Pattern Recognition in Bioinformatics*, Jun. 17-20, 2013, Nice, France.
Berland et al., "A new method for spectral characterization of protein families from sequence information using Fourier Transform," Abstract, *8th IAPR International Conference on Pattern Recognition in Bioinformatics*, Jun. 17-20, 2013, Nice, France.
Berland et al., "A new method for spectral characterization of protein families from sequence information using Fourier Transform," *Journées Ouvertes Biologie Informatique Mathématiques*, Toulouse, Jul. 1-4, 2013, pp. 186-187.
European Search Report completed Sep. 22. 2015 in related European Application No. 15305552.
Cosic, "Macromolecular bioactivity: Is it resonant interaction between macromolecules?—Theory and applications," IEEE Transactions on Biomedical Engineering, Dec. 1, 1994, vol. 41 No. 12, pp. 1101-1114.
Extended European Search Report for European Patent Application No. 15305552.0, dated Sep. 22, 2015.
"Coefficient of Determination", Wikipedia, as of Mar. 26, 2015, retrieved from https://en.wikipedia.org/w/index.php?title_Coefficient_of_determination&oldid=653639136.
"Fast Fourier Transform", Wikipedia, as of Apr. 7, 2015, retrieved from https://en.wikipedia.org/w/index.php?title=Fast_Fourier_transform&oldid=655315612.
"Root-mean-square Deviation", Wikipedia, as of Mar. 22, 2015, retrieved from https://en.wikipedia.org/w/index.php?title=Root-mean-square_deviation&oldid=653081433.
Berland "Exploration de meéthodes statistiques pour la modélisation de la relation séquence-activité de protéines d'intérét industriel", advertisement of thesis defense as retrieved from the website of the Université de La Réunion https://recherche.univ-reunion.fr/fileadmin/Fichiers/RECHERCHE/01_présentation/pdf/.

(Continued)

*Primary Examiner* — Mary K Zeman
(74) *Attorney, Agent, or Firm* — Knobbe Martens Olson & Bear, LLP

(57) ABSTRACT

A method for predicting at least one fitness value of a protein is implemented on a computer and includes the following steps: encoding the amino acid sequence of the protein into a numerical sequence according to a protein database, the numerical sequence comprising a value for each amino acid of the sequence; calculating a protein spectrum according to the numerical sequence; and for each fitness: comparing the calculated protein spectrum with protein spectrum values of a predetermined database, said database containing protein spectrum values for different values of said fitness, predicting a value of said fitness according to the comparison step.

14 Claims, 11 Drawing Sheets

Specification includes a Sequence Listing.

(56) References Cited

OTHER PUBLICATIONS

Berland et al. "A web-based tool for rational screening of mutants libraries using ProSAR", Protein Engineering, Design & Selection 27(10) 375-381 (2014).
Louis-Jeune et al., "Prediction of Protein Secondary Structure from Circular Dichroism Using Theoretically Derived Spectra", Proteins: Structure, Function, and Bioinformatics 80(2):374-381 (2012).
Murugan et al., "Cosic's Resonance Recognition Model for Protein Sequences and Photon Emission Differentiates Lethal and Non-Lethal Ebola Strains: Implications for Treatment", Open Journal of Biophysics 05(01):35-43 (Jan. 2015).
Nwankwo et al. "Digital Signal Processing Techniques: Calculating Biological Functionalities"—Norbert, Journal of Proteomics Bioinformation 4(12):260-268 (2011).
Veljkovic et al., "Discovery of New Therapeutic Targets by the Informational Spectrum Method", Current Protein and Peptide Science 9(5):493-506 (2008).
Printout from Université de la Reunion University Library (2020) showing unavailability of Thesis of Magali Berland, entitled "*Exploration of statistical methods for the modeling of sequence to activity relationship of proteins of industrial interest*".
Email dated Sep. 8, 2016 confirming extension of unavailability of Thesis of Magali Berland, entitled "*Exploration of statistical methods for the modeling of sequence to activity relationship of proteins of industrial interest*".
Letter dated Sep. 5, 2016 requesting extension of unavailability of Thesis of Magali Berland, entitled "*Exploration of statistical methods for the modeling of sequence to activity relationship of proteins of industrial interest*".
Registration Form dated Oct. 1, 2013 requesting delayed availability of Thesis of Magali Berland, entitled "*Exploration of statistical methods for the modeling of sequence to activity relationship of proteins of industrial interest*".
Pfander et al., "Periodic Wavelet Transforms and Periodicity Detection", *SIAM J. Appl. Math*., 62:1329-1368 (Abstract only) (2002).
Mohammed et al., "Developing Fast Techniques for Periodicity Analysis of Time Series", 2019 $3^{rd}$ International Symposium on Multidisciplinary Studies and Innovative Technologies (ISMSIT) (Abstract only) (Oct. 2019).

* cited by examiner

```
                        SEQUENCE LISTING

<160> NUMBER OF SEQ ID NOS: 3

<210> SEQ ID NO 1
    <211> LENGTH: 30
    <212> TYPE: PRT
    <213> ORGANISM: Artificial Sequence
    <220> FEATURE:
    <223> OTHER INFORMATION: synthetic peptide

<400> SEQUENCE: 1
```

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: synthetic peptide

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Ala Arg
            20                  25                  30

<210> SEQ ID NO 3
<211> LENGTH: 659
<212> TYPE: PRT
<213> ORGANISM: Homo sapiens

<400> SEQUENCE: 3

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Glu Arg Gln Ile Pro Arg
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala
        195                 200                 205

Ala Pro Val Ser Thr Ser Glu Leu Lys Lys Val Val Ala Leu Tyr Asp
    210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala

```
                260                 265                 270
Glu Asp Ser Ile Glu Met Tyr Glu Trp Tyr Ser Lys His Met Thr Arg
            275                 280                 285

Ser Gln Ala Glu Gln Leu Leu Lys Gln Glu Gly Lys Glu Gly Gly Phe
        290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
            325                 330                 335

Cys Ser Thr Pro Gln Ser Gln Tyr Tyr Leu Ala Glu Lys His Leu Phe
            340                 345                 350

Ser Thr Ile Pro Glu Leu Ile Asn Tyr His Gln His Asn Ser Ala Gly
            355                 360                 365

Leu Ile Ser Arg Leu Lys Tyr Pro Val Ser Gln Gln Asn Lys Asn Ala
        370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
            405                 410                 415

Lys Tyr Gly Lys Trp Arg Gly Gln Tyr Asp Val Ala Ile Lys Met Ile
            420                 425                 430

Lys Glu Gly Ser Met Ser Glu Asp Glu Phe Ile Glu Glu Ala Lys Val
            435                 440                 445

Met Met Asn Leu Ser His Glu Lys Leu Val Gln Leu Tyr Gly Val Cys
450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
            485                 490                 495

Gln Leu Leu Glu Met Cys Lys Asp Val Cys Glu Ala Met Glu Tyr Leu
        500                 505                 510

Glu Ser Lys Gln Phe Leu His Arg Asp Leu Ala Ala Arg Asn Cys Leu
    515                 520                 525

Val Asn Asp Gln Gly Val Val Lys Val Ser Asp Phe Gly Leu Ser Arg
530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
            565                 570                 575

Lys Ser Asp Ile Trp Ala Phe Gly Val Leu Met Trp Glu Ile Tyr Ser
            580                 585                 590

Leu Gly Lys Met Pro Tyr Glu Arg Phe Thr Asn Ser Glu Thr Ala Glu
        595                 600                 605

His Ile Ala Gln Gly Leu Arg Leu Tyr Arg Pro His Leu Ala Ser Glu
    610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
            645                 650                 655

Glu Glu Ser
```

METHOD AND ELECTRONIC SYSTEM FOR PREDICTING AT LEAST ONE FITNESS VALUE OF A PROTEIN, RELATED COMPUTER PROGRAM PRODUCT

CROSS REFERENCE TO RELATED APPLICATIONS

This application is the U.S. National Phase under 35 U.S.C. § 371 of International Application No. PCT/EP2016/058287, filed Apr. 14, 2016, designating the U.S., and published in English as WO 2016/166253 A1 on Oct. 20, 2016, which claims priority to European Patent Application No. 15305552.0, filed Apr. 14, 2015. The content of each of these related applications is incorporated herein by reference in its entirety.

REFERENCE TO SEQUENCE LISTING

The present application is being filed along with a Sequence Listing in electronic format. The Sequence Listing is provided as a file entitled Sequence_Listing_LAV-119.001APC.txt, created Oct. 14, 2016, which is 6,729 bytes in size. The information in the electronic format of the Sequence Listing is incorporated herein by reference in its entirety.

The present invention concerns a method and a related electronic system for predicting at least one fitness value of a protein, the protein comprising an amino acid sequence. The invention also concerns a non-transitory computer-readable medium comprising a computer program product including software instructions which, when implemented by a computer, implement such a method.

BACKGROUND OF THE INVENTION

Description of Related Art

Proteins are biological molecules consisting of at least one chain of amino acids sequence. Proteins differ from one another primarily in their sequence of amino acids, the differences between sequences being called "mutations".

One of the ultimate goals of protein engineering is the design and construction of peptides, enzymes, proteins or amino acid sequences with desired properties (collectively called "fitness"). The construction of modified amino acid sequences with engineered amino acid substitutions, deletions or insertions of amino acids or blocks of amino acids (chimeric proteins) (i.e. "mutants") allows an assessment of the role of any particular amino acid in the fitness and an understanding of the relationships between the protein structure and its fitness.

The main objective of the quantitative structure-function/fitness relationship analysis is to investigate and mathematically describe the effect of the changes in structure of a protein on its fitness. The impact of mutations is related to physico-chemical and other molecular properties of varying amino acids and can be approached by means of statistical analysis.

Exploring the fitness landscape, investigating all possible combinations (permutations) of n single point substitutions is a very difficult task. Indeed the number of mutants increases very quickly (Table 1).

TABLE 1

| Number of possible mutants for n mutations | |
|---|---|
| N° of single point mutations | N° of mutants |
| 2 | 4 |
| 4 | 16 |
| 6 | 64 |
| 8 | 256 |
| 10 | 1024 |
| 12 | 4096 |
| 14 | 16384 |
| 16 | 65536 |
| 40 | $1.1 \times 10^{12}$ |

Exploring all possible mutants is difficult experimentally, in particular when n increases. In practice, it is quite easy and cheap to produce mutants with single point substitutions in wet lab. For each of them, fitness can be readily characterized.

But combining single point substitutions is not so easy in wet lab. Generating all possible ($2^n$) combinations of targeted n single point substitutions can be very fastidious and costly. Evaluating fitness on large scale is problematic.

Mixed in vitro and in silico approaches have been developed to assist the process of directed evolution of proteins. They require from the wet lab to construct a library of mutants (by site-directed, random, or combinatorial mutagenesis), to retrieve the sequences and/or structures of a limited number of samples from library (called the "learning data set") and to assess fitness of each sampled mutant. They further require from the in silico to extract descriptors for each mutant, to use multivariate statistical method(s) for establishing relationship between descriptors and fitness (learning phase) and to establish a model to make predictions for mutants which are not experimentally tested.

A method based on 3D structure called Quantitative structure-function relationships (QFSR) has been proposed (Damborsky J, Prot. Eng. (1998) January; 11(1):21-30). Other methods, based only on sequence, not on 3D structure, and performing in silico rational screening using statistical modelling were proposed (Fox R. et al., Protein Eng. (2003) 16(8):589-97; Fox R., Journal of Theoretical Biology (2005), 234:187-199; Minshull J. et al., Curr Opin Chem Biol. 2005 April; 9(2):202-9; Fox R. et al., Nature Biotechnology (2007), 25(3):338-344; Fox R. and Huisman G W Trends Biotechnol. 2008 March; 26(3):132-8). The most known is ProSAR (Fox R., Journal of Theoretical Biology (2005), 234:187-199; Fox R. et al., Nature Biotechnology (2007), 25(3):338-344) which is based on a binary encoding (0 or 1).

The QSFR method is efficient and takes into account information about possible interactions with non-variants residues. However QSFR needs information on 3D protein structure, which is still currently limited, and the method is furthermore slow.

Comparatively, ProSAR does not need knowledge of 3D structure as it computed based on primary sequence only, and can use linear and non-linear models. However, ProSAR still suffers from drawbacks and its capacity of screening is limited. In particular, only those residues undergoing variation are included in the modelling and, as a consequence, information about possible interactions between mutated residues and other non-variant residues are missing. ProSAR relies on binary encoding (0 or 1) of the mutations which does not take into account the physico-chemical or other molecular properties of the amino acids. Additionally, (i) the new sequences that can be tested are only sequences with mutations, or combinations of mutations, at the positions that were used in the learning set used to build the model; (ii) the number of positions of mutations in the new sequences to be screened cannot be different from the number of mutations in the train set; and (iii) the calculation time when introducing non-linear terms in order to build a model is very long on a super computer (up to 2 weeks for 100 non-linear terms).

A versatile and fast in silico approach to help in the process of directed evolution of proteins is therefore still needed. The invention provides a method fulfilling these requirements and which is based on Digital Signal Processing (DSP).

Digital Signal Processing techniques are analytic procedures, which decompose and process signals in order to reveal information embedded in them. The signals may be continuous (unending), or discrete such as the protein residues. In proteins, Fourier transform methods have been used for biosequence (DNA and protein) comparison, characterization of protein families and pattern recognition, classification and other structure based studies such as analysis of symmetry and repeating structural units or patterns, prediction of secondary/tertiary structure prediction, prediction of hydrophobic core, motifs, conserved domains, prediction of membrane proteins, prediction of conserved regions, prediction of protein subcellular location, for the study of secondary structure content in amino acids sequence and for the detection of periodicity in protein. More recently new methods for the detection of solenoids domains in protein structures were proposed.

Digital Signal Processing techniques have helped analyse protein interactions (Cosic I., IEEE Trans Biomed Eng. (1994) 41(12):1101-14) and made biological functionalities calculable. These studies have been reviewed in detail in Nwankwo N. and Seker H. (J Proteomics Bioinform (2011) 4(12): 260-268).

In these approaches, protein residues are first converted into numerical sequences using one of the available AAindex from the database AAindex (Kawashima, S. and Kanehisa, M. Nucleic Acids Res. (2000), 28(1):374; Kawashima, S. et al., Nucleic Acids Res. January 2008; 36), representing a biochemical property or physico-chemical parameter for each amino acid. These numerical sequences are then processed by means of Discrete Fourier Transform (DFT) to present the biological characteristics of the proteins in the form of Informational Spectrum. This procedure is called Informational Spectrum Method (ISM) (Veljkovic V, et al., IEEE Trans Biomed Eng. 1985 May; 32(5):337-41). ISM procedure has been used to investigate principal arrangement in Calcium binding protein (Viari A, et al., Comput Appl Biosci. 1990 April; 6(2):71-80) and Influenza viruses (Veljkovic V., et al. BMC Struct Biol. 2009 April 7; 9:21, Veljkovic V., et al. BMC Struct Biol. 2009 September 28; 9:62).

A variant of the ISM, which engages amino acids parameter called Electron-Ion Interaction Potential (EIIP) is referred as Resonant Recognition Model (RRM). In this procedure, biological functionalities are presented as spectral characteristics. This physico-mathematical process is based on the fact that biomolecules with same biological characteristics recognise and bio-attach to themselves when their valence electrons oscillate and then reverberate in an electromagnetic field (Cosic I., IEEE Trans Biomed Eng. (1994) 41(12):1101-14; Cosic I., The Resonant Recognition Model of Macromolecular Bioactivity Birkhauser Verlag, 1997).

The Resonant Recognition Model involves four steps (see Nwankwo N. and Seker H., J Proteomics Bioinform (2011) 4(12): 260-268):

Step 1: Conversion of the Protein Residues into Numerical Values of Electron-Ion Interaction Potential (EIIP) Parameter.

Step 2: Zero-padding/Up-sampling. The process uses a zero padding to fill the gaps in the sequence of the proteins to be analysed at any position as signal processing requires that the window length of all proteins be the same.

Step 3: processing of the Numerical Sequences using Fast Fourier Transform (FFT) to yield Spectral Characteristics (SC) and point-wise multiplied to generate the Cross Spectral (CS) features during step 4.

Step 4: Cross-Spectral Analysis: Cross-Spectral (CS) analysis represents the point-wise multiplication of the Spectral Characteristics (SC).

Therefore the CS analysis has been used qualitatively, to predict, for instance, ligand-receptor binding based on common frequencies (resonance) between the ligand and receptor spectra. Another example is to predict a ras-like activity or not, i.e. ability or not to transform cells, by applying the RRM to Ha-ras p21 protein sequence.

The information provided by these prior art methods are useful, but are however insufficient to identify the most valuable protein mutants generated by directed evolution.

SUMMARY

The invention therefore relates to a method for predicting at least one fitness value of a protein, the method being implemented on a computer and including the following steps:

encoding the amino acid sequence of the protein into a numerical sequence according to a protein database, the numerical sequence comprising a value for each amino acid of the sequence;

calculating a protein spectrum according to the numerical sequence; and for each fitness:

comparing the calculated protein spectrum with protein spectrum values of a predetermined database, said database containing protein spectrum values for different values of said fitness, predicting a value of said fitness according to the comparison step.

Thus, the method developed by the inventors involves a quantitative analysis of the protein spectra which makes it possible to predict fitness values of proteins, and not only to predict the presence or not of a given activity.

According to other advantageous aspects of the invention, the method comprises one or more of the following features taken alone or according to all technically possible combinations:

the calculated protein spectrum includes at least one frequency value and the calculated protein spectrum is compared with said protein spectrum values for each frequency value;

during the protein spectrum calculation step, a Fourier Transform, such as a Fast Fourier Transform, is applied to the numerical sequence obtained further to the encoding step;

each protein spectrum verifies the following equation:

$$|f_j| = \left| \sum_{k=0}^{N-1} x_k \exp\left(\frac{-2i\pi}{N} jk\right) \right|$$

where j is an index-number of the protein spectrum $|f_j|$;
the numerical sequence includes N value(s) denoted $x_k$, with $0 \leq k \leq N-1$ and $N \geq 1$; and
i defining the imaginary number such that $i^2 = -1$;

during the encoding step, the protein database includes at least one index of biochemical or physico-chemical property values, each property value being given for a respective amino acid; and, for each amino acid, the value in the numerical sequence is equal to the property value for said amino acid in a given index;

during the encoding step, the protein database includes several indexes of property values; and the method further includes a step of selecting the best index based on a comparison of measured fitness values for sample proteins with predicted fitness values previously obtained for said sample proteins according to each index; the encoding step being then performed using the selected index;

during the selection step, the selected index is the index with the smallest root mean square error, wherein the root mean square error for each index verifies the following equation:

$$RMSE_{Index\_j} = \sqrt{\sum_{i=1}^{S} \frac{(y_i - \hat{y}_{i,j})^2}{S}}$$

where $y_i$ is the measured fitness of the $i^{th}$ sample protein,
$\hat{y}_{i,j}$ is the predicted fitness of the $i^{th}$ sample protein with the $j^{th}$ index, and
S the number of sample proteins;

during the selection step, the selected index is the index with the coefficient of determination nearest to 1, wherein the coefficient of determination for each index verifies the following equation:

$$R^2_{Index\_j} = \frac{\left(\sum_{i=1}^{S}(y_i - \bar{y})(\hat{y}_{i,j} - \bar{\hat{y}})\right)^2}{\sum_{i=1}^{S}(y_i - \bar{y})^2 \sum_{i=1}^{S}(\hat{y}_{i,j} - \bar{\hat{y}})^2}$$

where $y_i$ is the measured fitness of the $i^{th}$ sample protein,
$\hat{y}_{i,j}$ is the predicted fitness of the $i^{th}$ sample protein with the $j^{th}$ index,
S the number of sample proteins,
$\bar{y}$ is an average of the measured fitness for the S sample proteins, and
$\bar{\hat{y}}$ is an average of the predicted fitness for the S sample proteins;

the method further includes, after the encoding step and before the protein spectrum calculation step, the following step:
normalizing the numerical sequence obtained via the encoding step, by subtracting to each value of the numerical sequence a mean of the numerical sequence values;
the protein spectrum calculation step being then performed on the normalized numerical sequence;

the method further includes, after the encoding step and before the protein spectrum calculation step, the following step:
zero padding the numerical sequence obtained via the encoding step, by adding M zeros at one end of said numerical sequence, with M equal to (N–P) where N is a predetermined integer and P is the number of values in said numerical sequence;
the protein spectrum calculation step being then performed on the numerical sequence obtained further to the zero padding step;

the comparison step comprises determining, in the predetermined database of protein spectrum values for different values of said fitness, the protein spectrum value which is the closest to the calculated protein spectrum according to a predetermined criterion, the predicted value of said fitness being then equal to the fitness value which is associated in said database with the determined protein spectrum value;

during the protein spectrum calculation step, several protein spectra are calculated for said protein according to several frequency ranges, and
wherein, during the prediction step, an intermediate value of the fitness is estimated for each protein spectrum according to the comparison step, and the predicted value of the fitness is then computed using the intermediate fitness values,
preferably with a regression, such as a partial least square regression, on the intermediate fitness values; and the method includes a step of:
analysis of the protein according to the calculated protein spectrum, for screening of mutants libraries,
the analysis being done using preferably a factorial discriminant analysis or a principal component analysis.

The invention also relates to a non-transitory computer-readable medium comprising a computer program product including software instructions which, when implemented by a computer, implement a method as defined above.

The invention also relates to an electronic prediction system for predicting at least one fitness value of a protein, the prediction system including:
an encoding module configured for encoding the amino acid sequence into a numerical sequence according to a protein database, the numerical sequence comprising a value for each amino acid of the sequence;
a calculation module configured for calculating a protein spectrum according to the numerical sequence; and
a prediction module configured for, for each fitness:
comparing the calculated protein spectrum with protein spectrum values of a predetermined database, said database containing protein spectrum values for different values of said fitness, and
+predicting a value of said fitness according to said comparison.

BRIEF DESCRIPTION OF THE DRAWINGS

The invention will be better understood upon reading of the following description, which is given solely by way of example and with reference to the appended drawings, in which.

DETAILED DESCRIPTION

Figure 1:
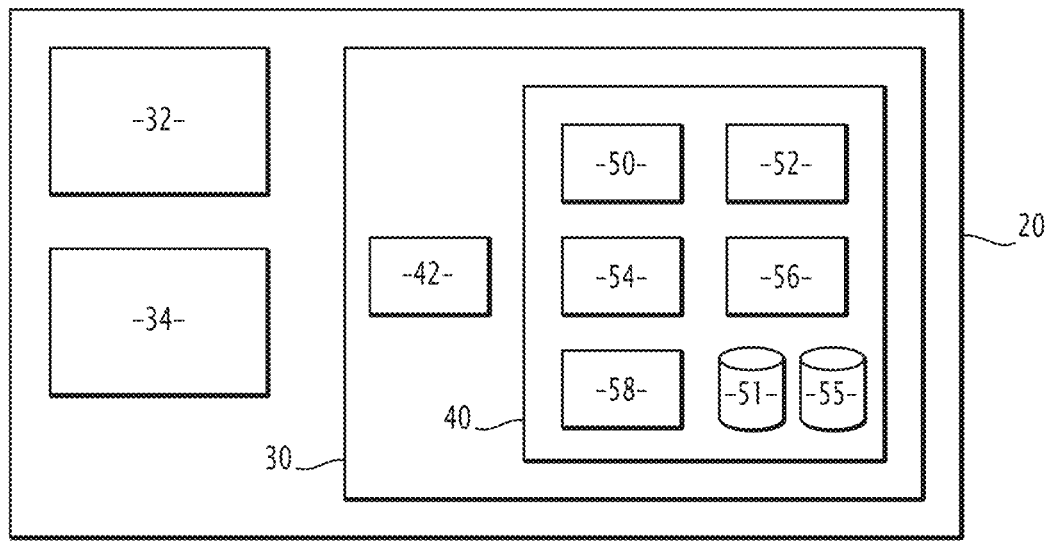
FIG. 1 is a schematic view of an electronic prediction system for predicting at least one fitness value of a protein, the prediction system including an encoding module configured for encoding the amino acid sequence into a numerical sequence, a calculation module configured for calculating a protein spectrum according to the numerical sequence; and a prediction module configured for predicting at least one value of each fitness.

By "protein", as used herein, is meant at least 2 amino acids linked together by a peptide bond. The term "protein" includes proteins, oligopeptides, polypeptides and peptides. The peptidyl group may comprise naturally occurring amino acids and peptide bonds, or synthetic peptidomimetic structures, i.e. "analogs", such as peptoids. The amino acids may either be naturally occurring or non-naturally occurring. In preferred embodiments, a protein comprises at least 10 amino acids, but less amino acids can be managed.

The "fitness" of a protein refers to its adaptation to a criterion, such as catalytic efficacy, catalytic activity, kinetic constant, Km, Keq, binding affinity, thermostability, solubility, aggregation, potency, toxicity, allergenicity, immunogenicity, thermodynamic stability, flexibility. According to the invention, the "fitness" is also called "activity" and it will be considered in the following of the description that the fitness and the activity refer to the same feature.

The catalytic efficacy is usually expressed in $s^{-1} \cdot M^{-1}$ and refers to the ratio kcat/Km. The catalytic activity is usually expressed in $mol \cdot s^{-1}$ and refers to the enzymatic activity level in enzyme catalysis.

The kinetic constant kcat is usually expressed in $s^{-1}$ and refers to the numerical parameter that quantifies the velocity of a reaction.

The Km is usually expressed in M and refers to the substrate concentration at which the velocity of reaction is half its maximum.

The Keq is usually expressed in (M, $M^{-1}$ or no unit) and quantity characterizing a chemical equilibrium in a chemical reaction, The binding affinity is usually expressed in M and refers to the strength of interactions between proteins or proteins and ligand (peptide or small chemical molecule).

The thermostability is usually expressed in ° C. and usually refers to the measured activity $T_{50}$ defined as the temperature at which 50% of the protein is irreversibly denatured after incubation time of 10 minutes.

The solubility is usually expressed in mol/L and refers to the number of moles of a substance (the solute) that can be dissolved per liter of solution before the solution becomes saturated.

The aggregation is usually expressed using aggregation Index (from a simple absorption measurement at 280 nm and 340 nm) and refers to the biological phenomenon in which mis-folded protein aggregate (i.e., accumulate and clump together) either intra- or extracellularly.

The potency is usually expressed in M and refers to the measure of drug activity expressed in terms of the amount required to produce an effect of given intensity.

The toxicity is usually expressed in M and refers to the degree to which a substance (a toxin or poison) can harm humans or animals.

The allergenicity is usually expressed in Bioequivalent Allergy Unit per mL (BAU/mL) and refers to the capacity of an antigenic substance to produce immediate hypersensitivity (allergy).

The immunogenicity is usually expressed as the unit of the amount of antibody in a sample and refers to the ability of a particular substance, such as an antigen or epitope, to provoke an immune response in the body of a human or animal The stability is usually expressed as AAG (kcal/mol−1) and refers to thermodynamic stability of a protein that unfolds and refolds rapidly, reversibly, and cooperatively.

The flexibility is usually expressed in A° and refers to protein disorder and conformational changes.

In FIG. 1, an electronic prediction system 20 for predicting at least one fitness value of a protein includes a data processing unit 30, a display screen 32 and input means 34 for inputting data into the data processing unit 30.

The data processing unit 30 is, for example, made of a memory 40 and a processor 42 associated to the memory 40.

The display screen 32 and the input means 34 are known per se.

The memory 40 is adapted for storing an encoding computer program 50 configured for encoding the amino acid sequence into a numerical sequence according to a protein database 51 and a calculation computer program 52 configured for calculating, according to the numerical sequence, a protein spectrum denoted hereinafter |f_j| with j an index-number of the protein spectrum.

The memory 40 is also adapted for storing a modeling computer program 54 configured for predetermining a protein spectra database 55 containing protein spectrum values for different values of said fitness.

The memory 40 is adapted for storing a prediction computer program 56 configured, for each fitness, for comparing the calculated protein spectrum with protein spectrum values of said predetermined database and for predicting a value of said fitness according to said comparison; and optionally further, for screening mutants libraries.

In optional addition, the memory 40 is adapted for storing a screening computer program 58 configured for analyzing the protein according to the calculated protein spectrum, thereby for screening mutants libraries, the analysis being preferably a factorial discriminant analysis or a principal component analysis.

The processor 42 is configured for executing each of the encoding, calculation, modeling, prediction and screening computer programs 50, 52, 54, 56, 58. The encoding, calculation, modeling, prediction and screening computer programs 50, 52, 54, 56, 58 form, when they are executed by the processor 42, respectively an encoding module for encoding the amino acid sequence into the numerical sequence according to the protein database; a calculation module for calculating the protein spectrum according to the numerical sequence; a modeling module for predetermining the database containing protein spectrum values; a prediction module for comparing the calculated protein spectrum with protein spectrum values of said predetermined database and for predicting a value of said fitness according to said comparison and for screening; and a screening module for analyzing the protein according to the calculated protein spectrum.

Alternatively, the encoding module 50, the calculation module 52, the modeling module 54, the prediction module 56 and the screening module 58 are in the form of programmable logic components, or in the form of dedicated integrated circuits.

The encoding module 50 is adapted for encoding the amino acid sequence into the numerical sequence according to the protein database 51, the numerical sequence comprising a value $x_k$ for each amino acid of the sequence. The numerical sequence is constituted of P value(s) $x_k$, with $0 \leq k \leq P-1$ and $P \geq 1$, k and P being integers.

The protein database 51 is, for example, stored in the memory 40. Alternatively, the protein database 51 is stored in a remote memory, not shown, which is distinct from the memory 40.

The protein database 51 is preferably the Amino Acid Index Database, also called AAIndex. Amino Acid Index Database is available from http://www.genome.jp/dbget-bin/www_bfind?aaindex (version Release 9.1, August 2006).

The protein database 51 includes at least one index of biochemical or physico-chemical property values, each property value being given for a respective amino acid. The protein database 51 includes preferably several indexes of biochemical or physico-chemical property values. Each index corresponds for example AAindex code, as it will be illustrated in the following in light of the respective examples. The chosen AAindex codes for encoding the amino acid sequence are for example: D Normalized frequency of extended structure, D Electron-ion interaction potential values, D SD of AA composition of total proteins, D pK-C or D Weights from the IFH scale.

For encoding the amino acid sequence, the encoding module 50 is then adapted to determine, for each amino acid, the property value for said amino acid in the given index, each encoded value $x_k$ in the numerical sequence being then equal to a respective property value.

In addition, in an optional manner, when the protein database 51 includes several indexes of property values; the encoding module 50 is further configured for selecting the best index based on a comparison of measured fitness values for sample proteins with predicted fitness values previously obtained for said sample proteins according to each index; and then for encoding the amino acid sequence using the selected index.

The selected index is, for example, the index with the smallest root mean square error, wherein the root mean square error for each index verifies the following equation:

$$RMSE_{Index\_j} = \sqrt{\sum_{i=1}^{S} \frac{(y_i - \hat{y}_{i,j})^2}{S}} \quad (1)$$

where $y_i$ is the measured fitness of the $i^{th}$ sample protein, $\hat{y}_{i,j}$ is the predicted fitness of the $i^{th}$ sample protein with the $j^{th}$ index, and S the number of sample proteins.

Alternatively, the selected index is the index with the coefficient of determination nearest to 1, wherein the coefficient of determination for each index verifies the following equation:

$$R^2_{Index\_j} = \frac{\left(\sum_{i=1}^{S}(y_i - \bar{y})(\hat{y}_{i,j} - \bar{\hat{y}})\right)^2}{\sum_{i=1}^{S}(y_i - \bar{y})^2 \sum_{i=1}^{S}(\hat{y}_{i,j} - \bar{\hat{y}})^2} \quad (2)$$

where $y_i$ is the measured fitness of the $i^{th}$ sample protein, $\hat{y}_{i,j}$ is the predicted fitness of the $i^{th}$ sample protein with the $j^{th}$ index, S the number of sample proteins, $\bar{y}$ is an average of the measured fitness for the S sample proteins, and is an average of the predicted fitness for the S sample proteins.

In addition, in an optional manner, the encoding module 50 is further configured for normalizing the obtained numerical sequence, for example by subtracting to each value $x_k$ of the numerical sequence a mean $\bar{x}$ of the numerical sequence values.

In other words, each normalized value, denoted $\tilde{x}_k$ verifies the following equation:

$$\tilde{x}_k = x_k - \bar{x} \quad (3)$$

The mean $\bar{x}$ is, for example, an arithmetic mean and satisfies:

$$\bar{x} = \frac{1}{P} \times \sum_{k=0}^{P-1} x_k \quad (4)$$

Alternatively, the mean $\bar{x}$ is a geometric mean, a harmonic mean or a quadratic mean.

In addition, in an optional manner, the encoding module 50 is further configured for zero-padding the obtained numerical sequence by adding M zeros at one end of said numerical sequence, with M equal to (N−P) where N is a predetermined integer and P is the initial number of values in said numerical sequence. N is therefore the total number of values in the numerical sequence after zero-padding.

The calculation module 52 is configured for calculating the protein spectrum according to the numerical sequence. The calculated protein spectrum includes at least one frequency value.

The calculation module 52 is configured for calculating the protein spectrum $|f_j|$, preferably by applying a Fourier Transform, such as a Fast Fourier Transform, to the obtained numerical sequence.

Each protein spectrum $|f_j|$ therefore verifies, for example, the following equation:

$$|f_j| = \left| \sum_{k=0}^{P-1} x_k \exp\left( \frac{-2i\pi}{P} jk \right) \right| \quad (5)$$

where j is an index-number of the protein spectrum $|f_j|$; and i defines the imaginary number such that $i^2 = -1$.

In addition, when the numerical sequence is normalized by the encoding module 50, the calculation module 52 is further configured for performing the protein spectrum calculation on the normalized numerical sequence.

In other words, in this case, each protein spectrum $|f_j|$ therefore verifies, for example, the following equation:

$$|f_j| = \left| \sum_{k=0}^{P-1} \tilde{x}_k \exp\left( \frac{-2i\pi}{P} jk \right) \right| \quad (6)$$

In addition, when zero-padding is performed on the numerical sequence by the encoding module 50, the calculation module 52 is further configured for calculating the protein spectrum $|f_j|$ on the numerical sequence obtained further to zero-padding.

In other words, in this case, each protein spectrum $|f_j|$ therefore verifies, for example, the following equation:

$$|f_j| = \left| \sum_{k=0}^{N-1} x_k \exp\left( \frac{-2i\pi}{N} jk \right) \right| \quad (7)$$

In addition, when both normalization and zero-padding are performed on the numerical sequence by the encoding module 50, the calculation module 52 is further configured for calculating the protein spectrum $|f_j|$ on the normalized numerical sequence obtained further to zero-padding.

In other words, in this case, each protein spectrum $|f_j|$ therefore verifies, for example, the following equation:

$$|f_j| = \left| \sum_{k=0}^{N-1} \tilde{x}_k \exp\left( \frac{-2i\pi}{N} jk \right) \right| \quad (8)$$

The modeling module 54 is adapted for predetermining the protein spectra database 55, also called model, according to learning data issued from the encoding module 50 and learning protein spectra issued from the calculation module 52. The learning protein spectra correspond to the learning data and the learning data are each related to a given fitness, and preferably for different values of said fitness.

The protein spectra database 55 contains protein spectrum values for different values of each fitness. Preferably, at least 10 protein spectra and 10 different fitness are used to build the protein spectra database 55. Of course, the higher are the number of protein spectra and related protein fitness; the better will be the results in terms of prediction of fitness. In the examples below the numbers of protein spectra and fitness used as learning data ranged from 8 to 242 (242 protein spectra and 242 protein fitness; 8 protein spectra and 8 protein fitness).

The prediction module 56 is adapted, for each fitness, for comparing the calculated protein spectrum with protein spectrum values of the protein spectra database 55 and for predicting a value of said fitness according to said comparison.

The prediction module 56 is further configured for determining, in the protein spectra database 55, the protein spectrum value which is the closest to the calculated protein spectrum according to a predetermined criterion, the predicted value of said fitness being then equal to the fitness value which is associated in the protein spectra database 55 with the determined protein spectrum value.

The predetermined criterion is, for example, the minimum difference between the calculated protein spectrum and the protein spectrum values contained in the protein spectra database 55. Alternatively, the predetermined criterion is the correlation coefficient R or determination coefficient R2 between the calculated protein spectrum and the protein spectrum values contained in the protein spectra database 55.

When the protein spectrum $|f_j|$ contains several frequency values, the calculated protein spectrum $|f_j|$ is compared with said protein spectrum values for each frequency value.

Alternatively, only some of the frequency values are taken into account for the comparison of the calculated protein spectrum $|f_j|$ with said protein spectrum values. In this case, frequency values are sorted for example according to their correlation with the fitness, and only the best frequency values are taken into account for the comparison of the calculated protein spectrum.

In addition, in an optional manner, the prediction module 56 is further configured for estimating an intermediate value of the fitness for each protein spectrum when several protein spectra are calculated for said protein according to several frequency ranges.

Then, the prediction module 56 is further configured for computing the predicted value of the fitness with a regression on said intermediate fitness values, such as a partial least square regression, also denoted PLSR.

Alternatively, the prediction module 56 is configured for computing the predicted value of the fitness using an Artificial Neural Network (ANN), with the input variables being said intermediate fitness values and the output variable being the predicted value of the fitness.

In addition, in an optional manner, the prediction module 56 allows obtaining a screening of mutants libraries, as it will be described in the following in view of FIG. 15 with the enantioselectivity as fitness.

Figure 16:
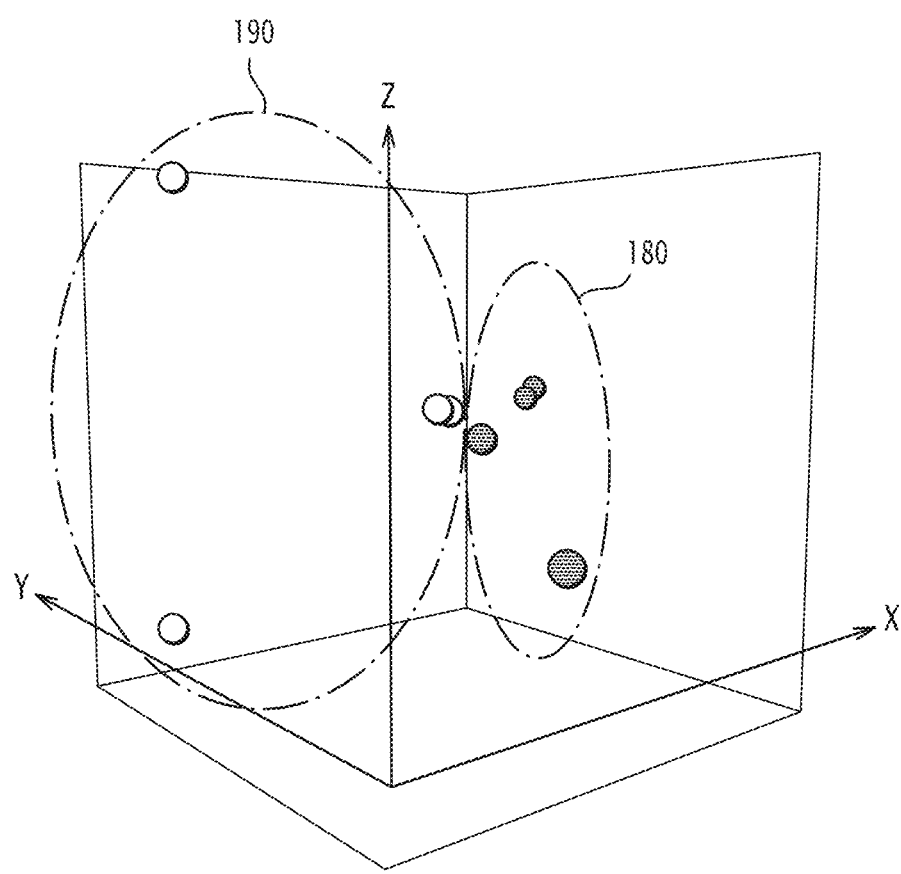
FIG. 16 represents a classification of protein spectra of 10 mutants of Epoxyde hydrolase using multivariate analysis (Principal Component Analysis) for protein screening.

In addition, in an optional manner, the screening module 58 is adapted for analyzing proteins according to the calculated protein spectra, and for classifying protein sequences according to their respective protein spectra using mathematical treatments, such as a factorial discriminant analysis or a principal component analysis followed for example by a k-means. The classification can be done for example to identify if in a family of protein spectra different groups exist: groups with high, intermediate and low fitness; a group with an expression of fitness and a group with no expression of fitness, as examples. In the following, this screening will be further illustrated in light of FIG. 16.

Figure 2:
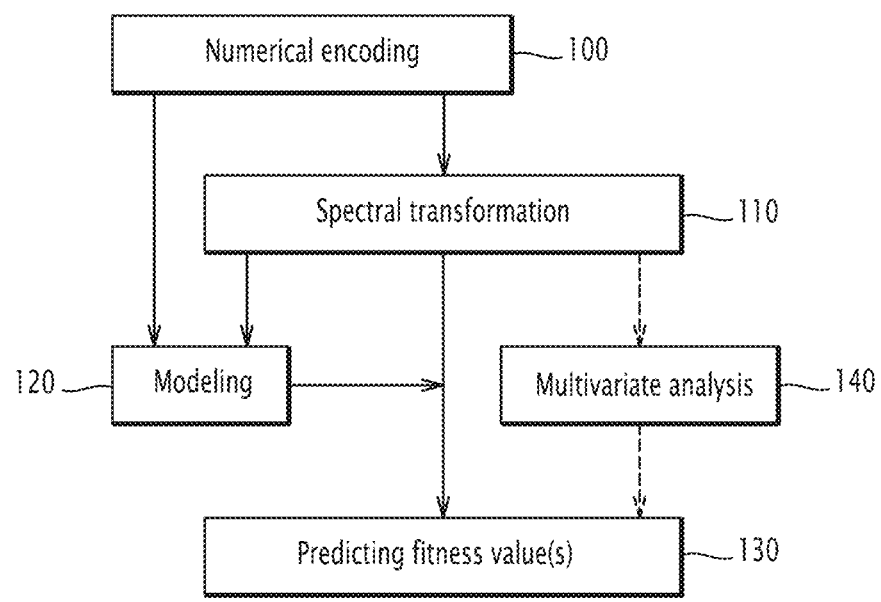
FIG. 2 is a schematic flow chart of a method for predicting at least one fitness value of a protein, according to the invention.

The operation of the electronic prediction system 20 according to the invention will now be described in view of FIG. 2 representing a flow chart of the method for predicting at least one fitness value of a protein.

In an initial step 100, the encoding module 50 encodes the amino acid sequence of the protein into the numerical sequence according to the protein database 51.

The encoding step 100 may be performed using the Amino Acid Index Database, also called AAIndex.

During the encoding step 100, the encoding module 50 determines, for each amino acid, the property value for said amino acid in the given index, for example in the given AAindex code, and then issues an encoded value $x_k$ which is equal to said property value.

In addition, when the protein database 51 optionally includes several indexes of property values; the encoding module 50 further selects the best index based on a comparison of measured fitness values for sample proteins with predicted fitness values previously obtained for said sample proteins according to each index; and then encodes the amino acid sequence using the selected index.

The best index is, for example, selected using equation (1) or equation (2). In addition, the encoding module 50 optionally normalizes the obtained numerical sequence, for example by subtracting to each value $x_k$ of the numerical sequence a mean $\bar{x}$ of the numerical sequence values according to equation (3).

In addition, the encoding module 50 optionally performs zero-padding on the obtained numerical sequence by adding M zeros at one end of said numerical sequence.

At the end of the encoding step 100, the encoding module 50 delivers learning numerical sequences and validation numerical sequences to the calculation module 52 and learning data to the modeling module 54.

Figure 3:
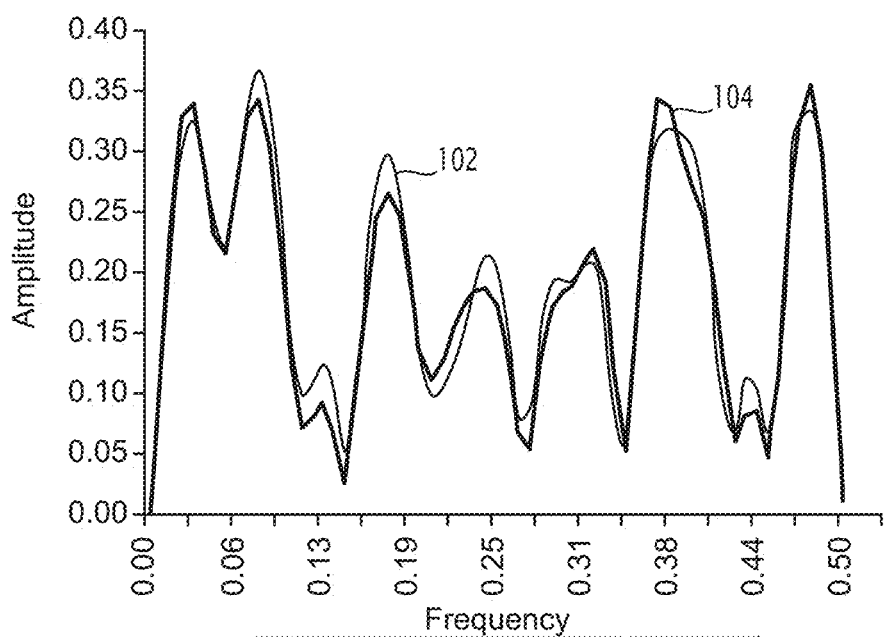
FIG. 3 represents curves of protein spectra obtained for native and mutant forms of human GLP1 protein.

An example of two protein spectra is shown in FIG. 3, with a first curve 102 represents the protein spectrum for the native form of human GLP1 protein and a second curve 104 represents the protein spectrum for the mutant form (single mutation) of human GLP1 protein. For each curve 102, 104, the successive discrete values of the protein spectrum are linked one to another.

In the next step 110, the calculation module 52 calculates a protein spectrum $|f_j|$ for each numerical sequence issued from the encoding module 50. The protein spectra corresponding to the learning numerical sequences are also called learning spectra and protein spectra corresponding to the validation numerical sequences are also called validation spectra. Step 110 is also called spectral transform step. The protein spectra $|f_j|$ are preferably calculated by using a Fourier Transform, such as a Fast Fourier Transform, for example according to an equation among the equations (5) to (8) depending on an optional normalization and/or zero-padding.

Then, the modeling module 54 determines, in step 120, the protein spectra database 55 according to learning data obtained during the encoding step 100 and learning protein spectra obtained during the spectral transform step 110.

In step 130, for each fitness, the prediction module 56 compares the calculated protein spectrum with protein spectrum values issued from the protein spectra database 55 and then predicts a fitness value according to said comparison.

More precisely, the prediction module 56 determines, in the protein spectra database 55, the protein spectrum value which is the closest to the calculated protein spectrum according to the predetermined criterion and the predicted fitness value is then equal to the fitness value which is associated with the determined protein spectrum value in the protein spectra database 55.

Optionally, only some of the frequency values are taken into account for the comparison of the calculated protein spectrum $|f_j|$ with said protein spectrum values.

In addition, the prediction module 56 estimates an intermediate fitness value for each protein spectrum when several protein spectra are optionally calculated for said protein according to several frequency ranges. Then, the prediction module 56 computes the predicted fitness value with a regression on said intermediate fitness values, such as a PLSR. Alternatively, the Artificial Neural Network (ANN) is used by the prediction module 56 for computing the predicted value of the fitness based on said intermediate fitness values. Then the prediction module 56 allows protein screening by ranking the protein spectra with regards to the predicted fitness.

Finally and optionally, the screening module 58 analyzes, in step 140, classifies protein sequences according to their respective protein spectra using mathematical treatments, such as a factorial discriminant analysis or a principal component analysis.

Alternatively, the analysis for screening of mutants libraries is operated directly on the calculated protein spectra, for example by using comparison with predetermined values.

It therefore allows obtaining a better screening of mutants libraries. This step is also called multivariate analysis step.

It should be noted that the analysis step 140 directly follows the spectral transform step 120 and that in addition the predicting step 130 may be performed after the analysis step 140 for predicting fitness values for some or all of the classified proteins.

Latent components are calculated as linear combinations of the original variables; the number of latent components is selected to minimize the RMSE (Root Mean Square Error).

Latent components are calculated as linear combinations of the original variables (the frequencies values); the number of latent components is selected to minimize the RMSE (Root Mean Square Error) by adding components one by one.

EXAMPLES

The invention will be further illustrated in view of the following examples.

Figure 4:
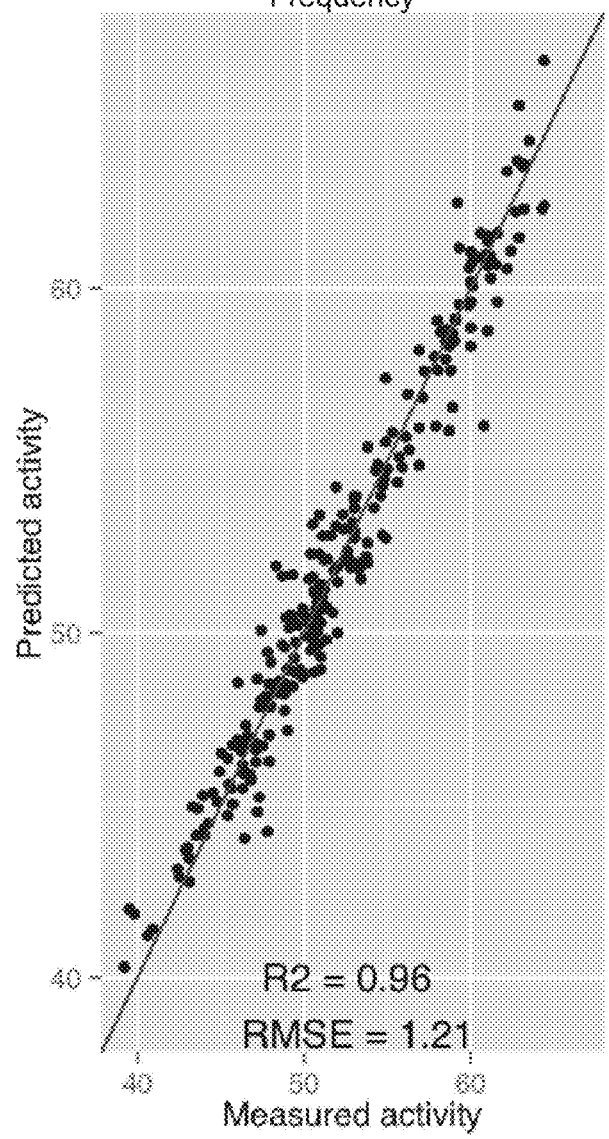
FIG. 4 is a set of points illustrating predicted and measured values of the thermostability for a set of proteins of the cytochrome P450 family, each point being related to a respective protein with the ordinate corresponding to the predicted value and the abscissa corresponding to the measured value, with the use of all the frequencies included in the protein spectra.
Figure 5:
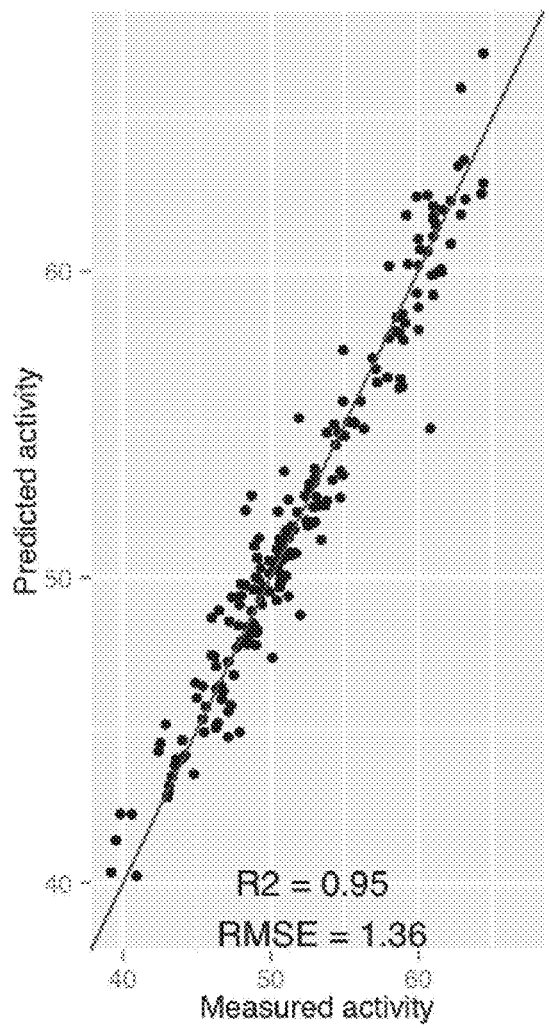
FIGS. 5 and 6 are views similar to that of FIG. 4, respectively obtained for training and validation subsets of the set of proteins from the cytochrome P450 family, the training subset being used for computing a database containing protein spectrum values for different values of the thermostability, and the validation subset being distinct from the training subset and used for testing the relevance of the predicted values in comparison with corresponding measured values.
Figure 6:
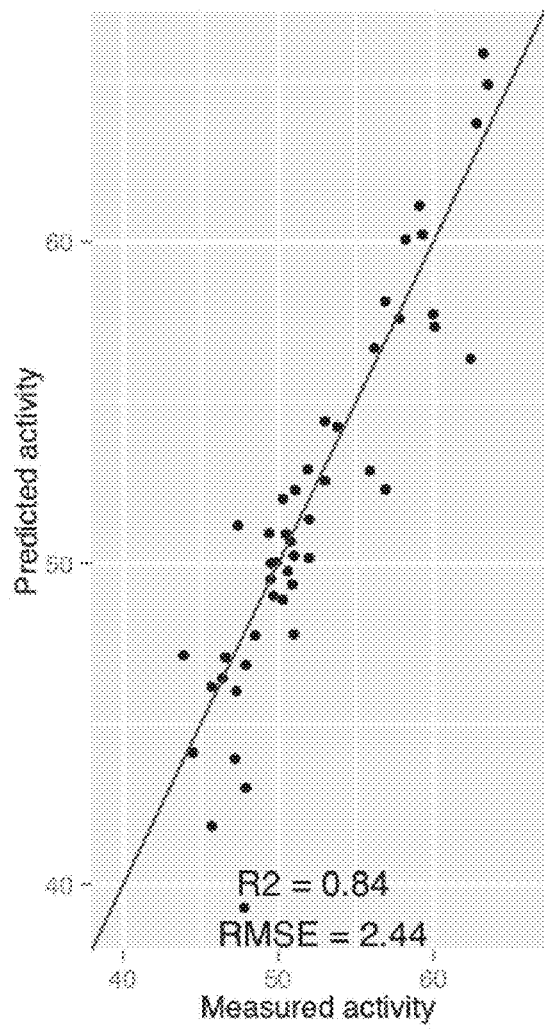

Example 1: Cytochrome P450 (FIGS. 4 to 6)

In this example, the amino acid sequence of cytochrome P450 was encoded into a numerical sequence using the following AAindex code: D Normalized frequency of extended structure (Maxfield and Scheraga, Biochemistry. 1976; 15(23):5138-53).

The first dataset (from Li et al., 2007: Nat Biotechnol 25(9):1051-1056.; Romero et al., PNAS. 2013: January 15, vol 110, n° 3: E193-E201) comes from a study around the sequence/stability-function relationship for the cytochrome P450 family, specifically the cytochrome P450 BM3 A1, A2 and A3, which aims to improve the thermostability of cytochromes. The versatile cytochrome P450 family of heme-containing redox enzymes hydroxylates a wide range of substrates to generate products of significant medical and industrial importance. New chimeric proteins were built with eight consecutive fragments inherited from any of these three different parents. The measured activity is the T50 defined as the temperature at which 50% of the protein is irreversibly denatured after an incubation time of 10 minutes. The out-coming dataset is made of 242 sequences of variants with T50 experimental values that ranged from 39.2 to 64.48° C. Recombination of the heme domains of CYP102A1, and its homologs CYP102A2 (A2) and CYP102A3 (A3), allows creating 242 chimeric P450 sequences made up of eight fragments, each chosen from one of the three parents. Chimeras are written according to fragment composition: 23121321, for example, represents a protein which inherits the first fragment from parent A2, the second from A3, the third from A1, and so on.

TABLE 2

CYTP450 Learning set

| Chimera | T50 | Chimera | T50 | Chimera | T50 |
|---|---|---|---|---|---|
| 22222222 | 43 | 21332223 | 48.3 | 31312133 | 52.6 |
| 32233232 | 39.8 | 21133313 | 50.8 | 23113323 | 51 |
| 31312113 | 45 | 12211232 | 49.1 | 22132331 | 53.3 |
| 23133121 | 47.3 | 21232233 | 50.6 | 11113311 | 51.2 |
| 21133312 | 45.4 | 12212332 | 48.4 | 32312231 | 52.6 |
| 11332233 | 43.3 | 31212323 | 48.7 | 22111223 | 51.3 |
| 12232332 | 39.2 | 32312232 | 49.1 | 21213231 | 54.9 |
| 22133232 | 47.9 | 21232332 | 49.3 | 21332312 | 52.9 |
| 22233221 | 46.8 | 22212322 | 50.7 | 22332211 | 53 |
| 23112323 | 46 | 31312212 | 48.9 | 22113323 | 53.8 |
| 12332233 | 47.1 | 22113332 | 48.7 | 22213132 | 52 |
| 32132233 | 42.9 | 31213332 | 50.8 | 22331223 | 51.7 |
| 22331123 | 47.9 | 22333332 | 49 | 23112233 | 51 |
| 21132222 | 45.6 | 22232331 | 50.5 | 22112223 | 52.8 |
| 23233212 | 39.5 | 21132321 | 49.3 | 32313231 | 52.5 |
| 32211323 | 46.6 | 22113223 | 49.9 | 22332223 | 52.4 |
| 32333233 | 47.2 | 22232233 | 49.6 | 22232333 | 53.7 |
| 23332331 | 48 | 22333211 | 50.7 | 31312332 | 54.9 |
| 21233132 | 42.4 | 23212212 | 49 | 21333221 | 51.3 |
| 32212231 | 47.4 | 23333213 | 50.1 | 23213333 | 56.1 |
| 23212212 | 48 | 23333131 | 50.5 | 21333233 | 54.2 |
| 22233211 | 46.3 | 22332233 | 49.9 | 21313112 | 54.8 |
| 31212321 | 44.9 | 11313233 | 48.3 | 31112333 | 55.7 |
| 32132232 | 42.5 | 21113322 | 50.4 | 31212331 | 51.8 |
| 22232322 | 45.4 | 31213233 | 50.6 | 23312323 | 53.8 |
| 31333233 | 46.5 | 23312121 | 49.3 | 22112323 | 55.3 |
| 12212212 | 44.8 | 32212232 | 48.8 | 31312323 | 52.3 |
| 22233212 | 44 | 11212333 | 50.4 | 22333231 | 53.1 |
| 22132113 | 40.6 | 23331233 | 50.9 | 23332231 | 51.4 |
| 22232222 | 47.5 | 22133323 | 49.4 | 31113131 | 54.9 |
| 23231233 | 45.5 | 22233323 | 48.4 | 21113133 | 51.9 |
| 11331312 | 43.5 | 21132323 | 50.1 | 21111323 | 54.4 |
| 33333233 | 46.3 | 12112333 | 50.9 | 23112333 | 54.3 |
| 22232123 | 43.1 | 12211333 | 50.6 | 23313233 | 56.3 |
| 22212123 | 47.7 | 21313122 | 50.5 | 22132231 | 53 |
| 23113112 | 46.3 | 21132212 | 48.8 | 22113232 | 51.1 |
| 12213212 | 44 | 21332322 | 48.8 | 22112211 | 54.7 |
| 23132233 | 43.6 | 32212323 | 48.4 | 33312333 | 54.7 |
| 23133233 | 43.1 | 21333223 | 49.1 | 22312111 | 53 |
| 23332223 | 46.7 | 23213232 | 48.5 | 21212321 | 53.3 |
| 31212212 | 47.1 | 22333321 | 49.2 | 12313331 | 51.2 |
| 21232212 | 47.8 | 21332112 | 50.4 | 22312311 | 55.6 |
| 11331333 | 46.3 | 32212233 | 49.9 | 21312323 | 61.5 |
| 21232321 | 46 | 22113111 | 49.2 | 21212333 | 63.2 |
| 21133232 | 46.4 | 23212211 | 50.7 | 22313323 | 60 |
| 23132231 | 48 | 23313323 | 50.9 | 22313233 | 58.5 |
| 12232232 | 40.9 | 11111111 | 55 | 31311233 | 56.9 |
| 21132112 | 47.1 | 32313233 | 52.9 | 31312233 | 57.9 |
| 23133311 | 44.2 | 22312322 | 54.6 | 21332233 | 58.9 |
| 22232212 | 46.2 | 21212112 | 51.2 | 21332131 | 58.5 |
| 33333333 | 49 | 11312233 | 51.6 | 21313313 | 64.4 |
| 21133233 | 48.8 | 31212332 | 53.4 | 23313333 | 61.2 |
| 21212111 | 57.2 | 21313333 | 62.9 | 22311331 | 58.9 |
| 21333333 | 58 | 21312313 | 62.2 | 21312133 | 60.1 |
| 21212231 | 59.9 | 21311233 | 62.7 | 22311233 | 60.9 |
| 22313232 | 58.8 | 21313331 | 62.2 | 21311311 | 61 |
| 21312123 | 60.8 | 22312331 | 59.3 | 22313331 | 58.5 |
| 21311331 | 62.9 | 22312233 | 61 | 21112333 | 61.6 |
| 21313231 | 61 | 21313233 | 60 | 22313231 | 59 |
| 22312133 | 57.1 | 21312311 | 59.1 | 21212233 | 60 |
| 22312231 | 60 | 22313333 | 64.3 | 21112331 | 61.6 |
| 21312333 | 64.4 | 21311313 | 61.2 | 21112233 | 58.7 |
| 21312331 | 60.6 | 21312213 | 60.6 | 22112333 | 58 |
| 21311333 | 59.2 | 21312332 | 59.9 | 21113333 | 61 |
| 21312233 | 63.1 | 22312313 | 61 | 22112233 | 58.7 |

FIG. 4 show results obtained after performing a model on the whole collection of protein sequences using a leave one out cross validation (LOOCV) R2=0.96 and RMSE=1.21. This demonstrates that information relative to the fitness of the protein can be captured using such a method.

TABLE 3

CYTP450 test set

| Chimera | T50 | Chimera | T50 | Chimera | T50 |
|---|---|---|---|---|---|
| 11332212 | 47.8 | 31313232 | 51.9 | 22213223 | 50.8 |
| 32332231 | 49.4 | 23332221 | 46.4 | 21331332 | 52 |
| 23313111 | 56.9 | 22111332 | 50.9 | 11313333 | 53.8 |
| 23333311 | 45.7 | 22332222 | 50.3 | 32311323 | 52 |
| 31331331 | 47.3 | 21131121 | 53 | 23132311 | 44.5 |
| 21231233 | 50.6 | 21232232 | 49.5 | 21333211 | 55.9 |
| 21112122 | 50.3 | 31212232 | 51 | 32312333 | 57.8 |
| 22113311 | 51.1 | 23213211 | 47.4 | 22312332 | 59.1 |
| 23333233 | 51 | 32232131 | 43.9 | 22312333 | 63.5 |
| 13333211 | 45.7 | 22133212 | 47.2 | 12322333 | 47.9 |
| 23213311 | 49.5 | 21313311 | 56.9 | 21312231 | 62.8 |
| 32332233 | 48.5 | 21332231 | 60 | 22311333 | 60.1 |
| 22213212 | 50.5 | 21113312 | 53 | 21311231 | 63.2 |
| 22132212 | 46.6 | 22312223 | 56.2 | 21312211 | 59.3 |
| 21111333 | 62.4 | 22232121 | 49.7 | 22213333 | 58.2 |
| 32113232 | 47.9 | 31332233 | 49.9 | | |

FIGS. 5 and 6 give the capacity of the model to predict combination of mutations for cytochrome P450. Here, the dataset was split in 196 sequences as learning sequences and 46 as validation sequences.

Figure 7:
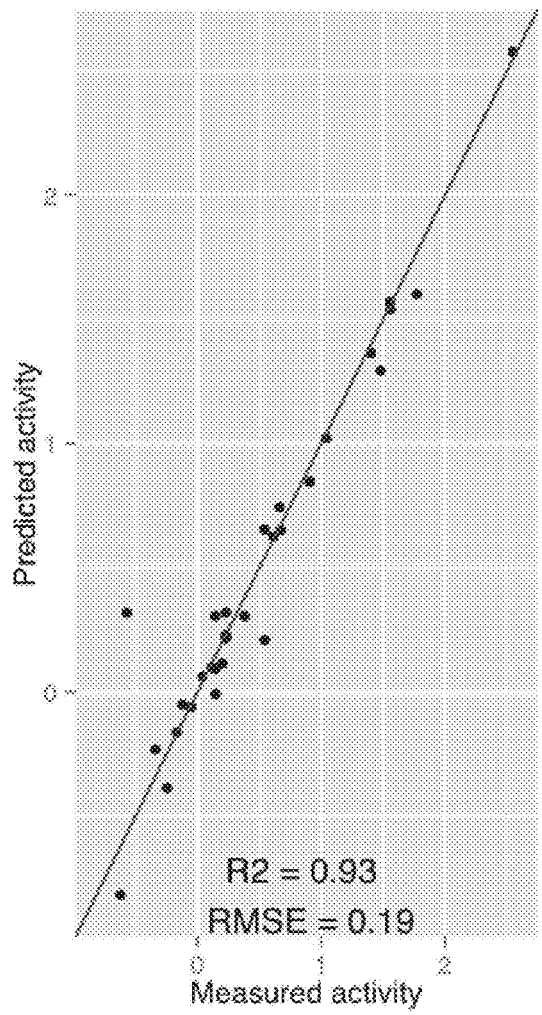
FIG. 7 is a view similar to that of FIG. 4 with predicted and measured values of the binding affinity for a set of GLP1 mutants.
Figure 8:
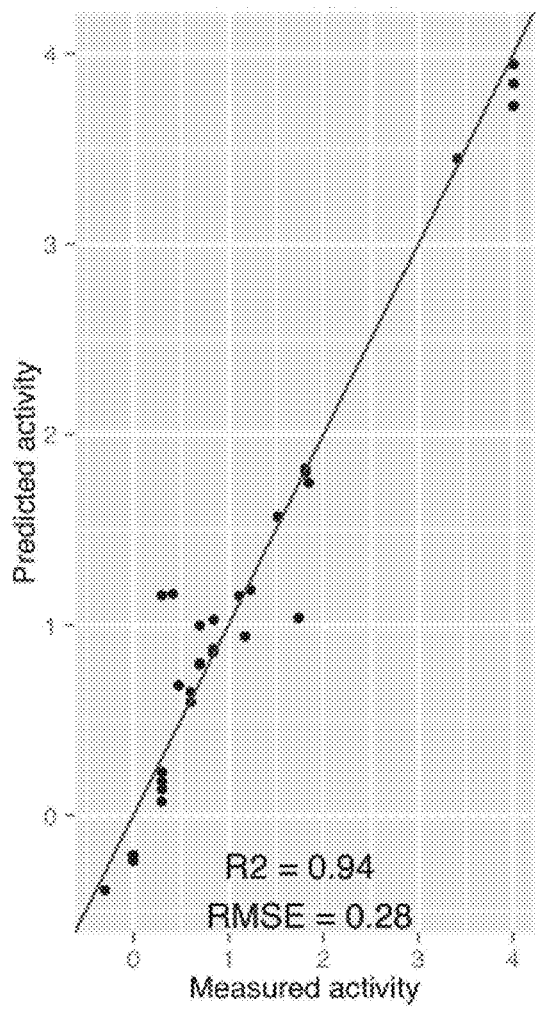
FIG. 8 is a view similar to that of FIG. 4 with predicted and measured values of the potency for a set of GLP1 mutants.

Example 2: Human Glucagon-Like Peptide-1 (GLP1) Predicted Analogs (FIGS. 7 and 8)

In this example, the amino acid sequence of GLP1 was encoded into a numerical sequence using the following AAindex code: D Electron-ion interaction potential values (Cosic, IEEE Trans Biomed Eng. 1994 December; 41(12): 1101-14.).

Taspoglutide and Extendin-4 are GLP1 analogs that act as peptide agonists of the glucagon-like peptide (GLP) receptor and that are under clinical development (Taspoglutide) for the treatment of type II diabetes mellitus.

```
Human GLP1
                              (SEQ ID NO: 1)
HAEGTFTSDVSSYLEGQAAKEFIAWLVKGR Taspoglutide
                              (SEQ ID NO: 2)
HAEGTFTSDVSSYLEGQAAKEFIAWLVKAR
```

The method of the invention has been implemented to provide candidate agonists of GLP1 receptor that improve binding affinity (interaction with receptor) and/or improve potency (activation of receptor-adenylyl cyclase activity) with respect to native human GLP1 and taspoglutide.

Starting for the sequence of human GLP1, a library of mutants has been designed in silico by performing single point site saturation mutagenesis: every position of the amino acid sequence is substituted with the 19 other natural amino acids. Hence if the protein sequence is composed of n=30 amino acids, the generated library will comprise of 30×19=570 single point variants. Combinations of single point mutations have been run.

Adelhorst K et al. (J Biol Chem. 1994 Mar. 4; 269(9): 6275-8) previously described a series of analogs of GLP-1 made by Ala-scanning, i.e. by replacing each amino acid successively with L-alanine, to identify side-chain functional groups required for interaction with the GLP-1 receptor. In the case of L-alanine being the parent amino acid, substitution had been made with the amino acid found in the corresponding position in glucagon. These analogs had been assayed in binding assays (IC50) against rat GLP-1 receptor, and potency (receptor activation measured by detection of adenylate cyclase activity, EC50) had further been monitored. These analogs (30 single mutants) and their reported activities (Log(IC50) and Log(EC50) normalized compared to IC50 or EC50, respectively, of wild-type human GLP1) were used as learning data set to build the predictive model (see FIG. 7 and FIG. 8).

TABLE 4

| GLP1 Learning set | | |
| --- | --- | --- |
| Peptide | logIC50 | logEC50 |
| Wild-type GLP1 | −0.56864 | |
| GLP1 F6A | | 1.51851 |
| GLP1 S8A | −0.11919 | 0.69897 |
| GLP1 D9A | | 4 |
| GLP1 S11A | −0.33724 | 0.47712 |
| GLP1 S12A | −0.16749 | 0.30103 |
| GLP1 Y13A | | 1.74036 |

TABLE 4-continued

| GLP1 Learning set | | |
| --- | --- | --- |
| Peptide | logIC50 | logEC50 |
| GLP1 L14A | | 0.8451 |
| GLP1 E15A | | 1.81291 |
| GLP1 G16A | −0.24413 | 0.60206 |
| GLP1 Q17A | | 0.69897 |
| GLP1 A18R | −0.05061 | 1.23045 |
| GLP1 E21A | −0.61979 | 0 |
| GLP1 V10A | 0.23045 | |
| GLP1 K20A | 0.14613 | 1.11394 |
| GLP1 A24Q | 0.14613 | −0.30103 |
| GLP1 W25A | 0.20412 | |
| GLP1 L26A | | 0.60206 |
| GLP1 V27A | 0.14613 | |
| GLP1 W25A | | 1.17609 |
| GLP1 K28A | 0.23045 | 0.30103 |
| GLP1 G29A | 0.11394 | 0 |
| GLP1 R30A | | 0.8451 |
| GLP1 A2S | 0.38021 | 0.30103 |
| GLP1 Y13A | 0.54407 | |
| GLP1 E15A | 0.61278 | |
| GLP1 L26A | 0.6721 | |
| GLP1 R30A | 0.66276 | |
| GLP1 H1A | 1.47712 | 4 |
| GLP1 E3A | 0.90849 | 0.30103 |
| GLP1 G4A | 1.77085 | 4 |
| GLP1 T5A | | 0.69897 |
| GLP1 F6A | 1.5563 | |
| GLP1 T7A | 1.5563 | 1.81291 |
| GLP1 D9A | 1.04139 | 4 |
| GLP1 I23A | 1.39794 | 1.8451 |

TABLE 5

| GLP1 test sequences (binding) | |
| --- | --- |
| Test peptide | logIC50 |
| GLP1 T5A | 0.54407 |
| GLP1 L14A | 0.23045 |
| GLP1 Q17A | 0.04139 |
| GLP1 F22A | 2.54531 |

TABLE 6

| GLP1 test sequences (potency) | |
| --- | --- |
| Test peptide | logEC50 |
| GLP1 V10A | 0.8451 |
| GLP1 F22A | 3.41497 |
| GLP1 V27A | 0.30103 |
| Wild-type GLP1 | 0.41497 |

Their activity ranged from −0.62 to 2.55 (log IC50) for the binding affinity and from −0.30 to 4.00 (log EC50) for the Potency.

Results show that R2 and RMSE are 0.93 and 0.19 respectively for the Binding affinity (FIG. 7) and 0.94 and 0.28 for the Potency (FIG. 8), thus indicating that information relative to the two fitnesses can be captured in a very efficient way.

Binding and potency evaluated for human GLP1, taspoglutide and the best in silico analog (based on the predictive model) were as shown in Table 7:

TABLE 7 binding and potency evaluated for human GLP1 and analogs

|  | Binding (IC50) nM | Potency (EC50) nM |
|---|---|---|
| Human GLP1 | 0.27 | 2.6 |
| taspoglutide | 0.79 | 0.39 |
| best in silico analog | 0.002 | 0.021 |

A 135 times improvement is achieved for binding affinity for the peptidic ligand analog of GLP1 towards his receptor. A 124 times potency improvement is obtained.

This illustrates that the method of the invention can be used to improve more than one parameter at the same time.

Figure 14:
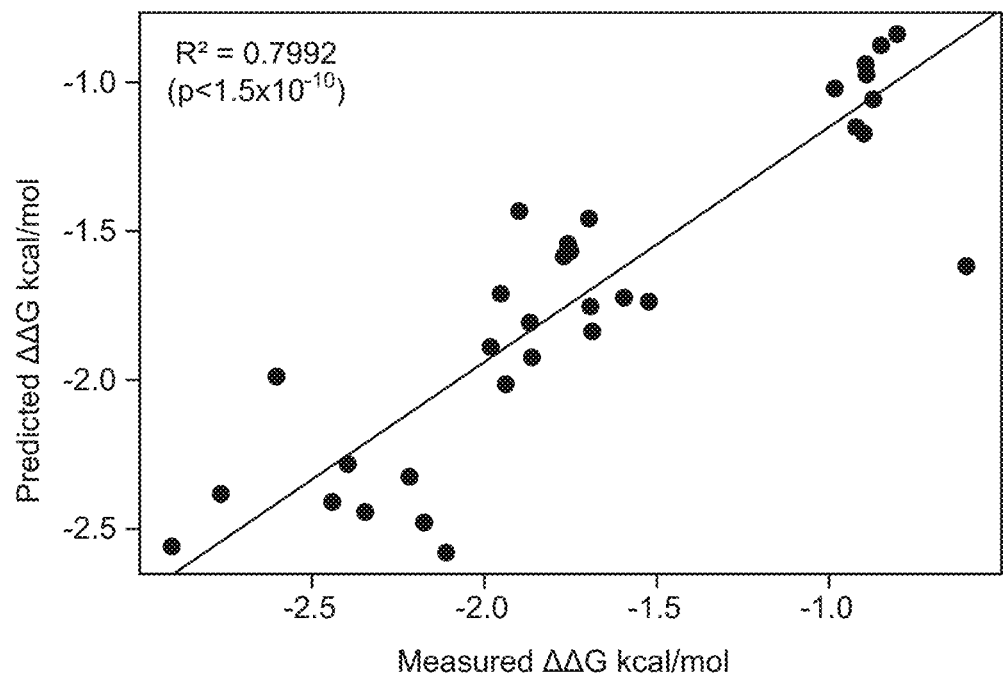
FIG. 14 is a view similar to that of FIG. 4 with predicted and measured values of the enantioselectivity for a set of proteins of an epoxide hydrolase family.

Example 3: Evolution of the Enantioselectivity of an Epoxide Hydrolase (FIGS. 14 and 15)

In this example, the amino acid sequence of epoxide hydrolase was encoded into a numerical sequence using the following AAindex code: D SD of AA composition of total proteins (Nakashima et al., Proteins. 1990; 8(2):173-8).

Enantioselectivity is the preferential formation of one stereoisomer over another, in a chemical reaction. Enantioselectivity is important for synthesis of many industrially relevant chemicals, and is difficult to achieve. Green chemistry takes advantage of recombinant enzymes, as enzymes have high specificities, to synthesize chemical products of interest. Enzymes with improved efficiencies are therefore particularly sought in green chemistry.

Reetz, et al. (Ang 2006 Feb. 13; 45(8):1236-41) described directed evolution of enantioselective mutants of the epoxide hydrolase from *Aspergillus niger* as catalysts in the hydrolytic kinetic resolution of the glycidyl ether 1 with formation of diols (R)- and (S)-2.

The model was built on a set of 10 learning sequences described in Reetz et al. (supra).

TABLE 8 learning set

| epoxide hydrolase | ΔΔG (kcal/mol) |
|---|---|
| WT | −0.85 |
| L215F | −1.50 |
| A217N | −1.17 |
| R219S | −0.85 |
| L249Y | −0.85 |
| T317W | −1.50 |
| T318V | −0.85 |
| M329P | −1.08 |
| L330Y | −0.85 |
| C350V | −0.97 |

The results for 32 mutants produced in wet lab have been compared to those predicted using our approach. Quantitative values are shown on the right of the FIG. 14: with representation of both experimental and predictive values. The predictive values obtained are very close to the experimental ones, with a mean bias of −0.011 kcal/mol. This demonstrates that even on a small number of learning sequences and learning data, good mutants with improved parameters can be obtained.

Figure 15:
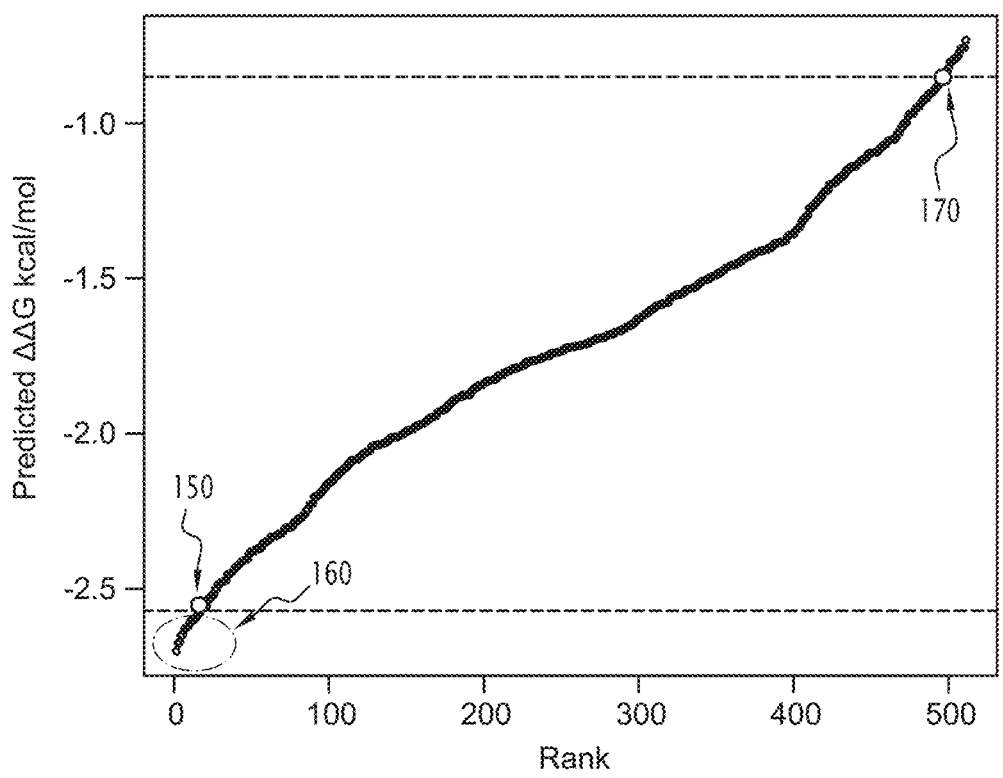
FIG. 15 represents a screening of a library of of 512 mutants of Epoxide hydrolase.

In FIG. 15, the library of 512 mutants was built and screened. The best mutant identified in the wet lab appears indeed to be a good one (arrow 150), but not the best. The best ones are identified by the ellipse 160 in FIG. 15. The wild-type protein is pointed by arrow 170.

TABLE 9 test sequences

| epoxide hydrolase | ΔΔG (kcal/mol) |
|---|---|
| WT | −0.85 |
| L215F_A217N_R219S | −1.68 |
| M329P_L330Y | −0.87 |
| C350V | −0.89 |
| L249Y | −0.8 |
| T317W_T318V | −1.68 |
| L215F_A217N_R219S_M329P_L330Y | −1.84 |
| L215F_A217N_R219S_C350V | −1.67 |
| L215F_A217N_R219S_T317W_T318V | −2.19 |
| L215F_A217N_R219S_L249Y | −1.93 |
| M329P_L330Y_C350V | −0.9 |
| T317W_T318V_M329P_L330Y | −0.6 |
| L249Y_M329P_L330Y | −0.98 |
| T317W_T318V_C350V | −1.73 |
| L249Y_C350V | −0.89 |
| L249Y_T317W_T318V | −1.88 |
| L215F_A217N_R219S_T317W_T318V_M329P_L330Y | −2.15 |
| L215F_A217N_R219S_L249Y_M329P_L330Y | −1.96 |
| L215F_A217N_R219S_T317W_T318V_C350V | −2.41 |
| L215F_A217N_R219S_L249Y_C350V | −1.85 |
| L215F_A217N_R219S_L249Y_T317W_T318V | −2.37 |
| T317W_T318V_M329P_L330Y_C350V | −1.51 |
| L249Y_M329P_L330Y_C350V | −0.92 |
| L249Y_T317W_T318V_M329P_L330Y | −1.75 |
| L249Y_T317W_T318V_C350V | −1.74 |
| L215F_A217N_R219S_L249Y_M329P_L330Y_C350V | −2.57 |
| L215F_A217N_R219S_T317W_T318V_M329P_L330Y_C350V | −2.09 |
| L215F_A217N_R219S_L249Y_T317WT318VM329P_L330Y | −2.32 |
| L215F_A217N_R219S_L249Y_T317W_T318V_C350V | −2.73 |
| T317W_T318V_M329P_L330Y_C350V | −1.58 |
| L215F_A217N_R219S_L249Y_T317W_T318V_M329P_L330Y_C350V | 2.87 |
| L215F_A217N_R219S_M329P_L330Y_C350V | −1.92 |

Figure 9:
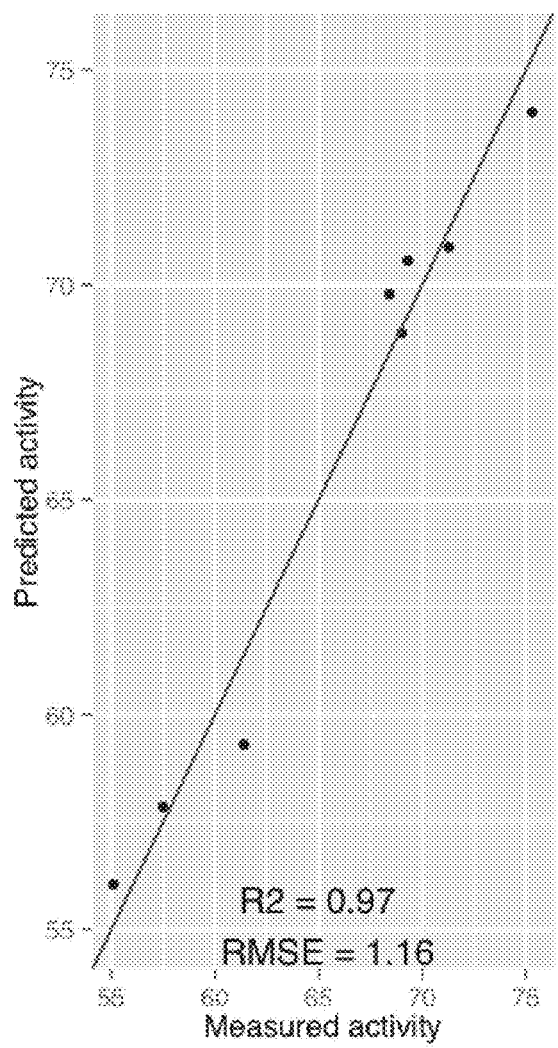
FIGS. 9 and 10 are views similar to that of FIG. 4 with predicted and measured values of the thermostability, respectively obtained for training and validation subsets of a set of Enterotoxins SEE and SEA, the training subset being used for computing a database containing protein spectrum values for different values of said thermostability, and the validation subset being distinct from the training subset and used for testing the relevance of the predicted values.
Figure 10:
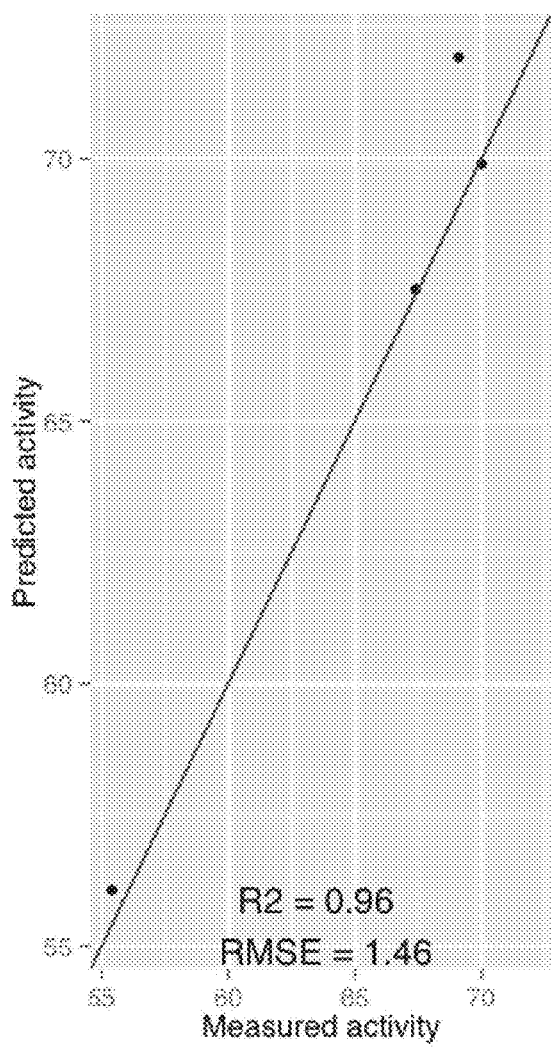

Example 4: Prediction of the Thermostability (Tm) for the Enterotoxins SEA and SEE (FIGS. 9 and 10)

In this example, the amino acid sequence of enterotoxins was encoded into a numerical sequence using the following AAindex code: D pK-C (Fasman, 1976)

The fourth dataset (from Cavallin A. et al., 2000: Biol Chem. January 21; 275(3):1665-72.) is related to the thermostability of enterotoxins SEE and SEA. Super-antigens (SAgs), such as the staphylococcal enterotoxins (SE), are very potent T-cell-activating proteins known to cause food poisoning or toxic shock. The strong cytotoxicity induced by these enterotoxins has been explored for cancer therapy by fusing them to tumour reactive antibodies. The Tm is defined as the denaturation temperatures EC50 value and ranged from 55.1 to 73.3° C. for a dataset constituted of 12 protein sequences (WT SAE+WT SEE+10 mutants included form 1 single to 21 multiple mutations).

TABLE 10

Details of the mutations regions for SEA and SEE. SEE/A-a, -f, -h, and -ah are SEE with the regions a, f, a and a + h, respectively, from SEA, whereas SEA/E-bdeg is SEA with the regions b + d + e + g from SEE.

| Mutations regions | Superantigens staphylococcal enterotoxin | |
|---|---|---|
| | Mutations for SEA | Mutations for SEE |
| a (20-27) | G20R, T21N, G24S, K27R | R20G, N21T, S24G, R27K |
| b (37-50) | K37I, H44D, Q49E, H50N | I37K, D44H, E49Q, N50H |
| c (60-62) | D60G, S62P | G60D, P62S |
| d (71-78) | F71L, D72G, I76A, V77T, D78N | L71F, G72D, A76I, T77V, N78D |
| e (136-149) | N136T, L140I, E141D, T142K, N146S, N149E | T136N, I140L, D141E, K142T, S146N, E149N |
| f (161-176) | R161H, Q164H, E165G, Y167F, N168G, V174S, D176G | H161R, H164Q, G165E, F167Y, G168N, S174V, G176D |
| g (188-195) | T188S, T190E, E191G, P192S, S193T, N195S | S188T, E190T, G191E, S192P, T193S, S195N |
| h (200-207) | G200D, S206P, N207D | D200G, P206S, D207N |

TABLE 11 learning set

| Enterotoxin | Tm |
|---|---|
| SEA_D227A | 55.1 |
| SEA_H187A | 57.5 |
| SEA_233aa (wild-type) | 61.4 |
| SEA/E-bdeg | 68.4 |
| SEE/A-h | 69 |
| SEE/A-a_D227A | 69.3 |
| SEE_233aa (wild-type) | 71.3 |
| SEE/A-a | 75.3 |

TABLE 12 test sequences

| Enterotoxin | Tm |
|---|---|
| SEE_A-f | 70 |
| SEE_A-ah | 69.1 |
| SEE_D227A | 67.4 |
| SEA_D227A_F47A | 55.4 |

Our predictions were compared to wet lab results (Cavallin A. 2000). Here again, using a small learning sequence (8 learning sequences) and learning data, it was possible to capture the information linked to the thermostability and to predict this parameter for new mutants.

It should be noted that among the protein sequences of the validation set corresponding to FIG. 10 (4 protein sequences), 2 included mutations in positions that were not sampled in the training set corresponding to FIG. 9 (1 sequence with 7 new mutations, and 1 sequence avec 1 new mutation over 2). So, these results confirm that it is possible to identify new mutants including positions of mutations that have not been sampled in the training set.

Results show that R2 and RMSE are 0.97 and 1.16 respectively for the training set (FIG. 9) and 0.96 and 1.46 for the validation set (FIG. 10), thus indicating that information relative to the thermostability can be efficiently predicted in this case.

Figure 11:
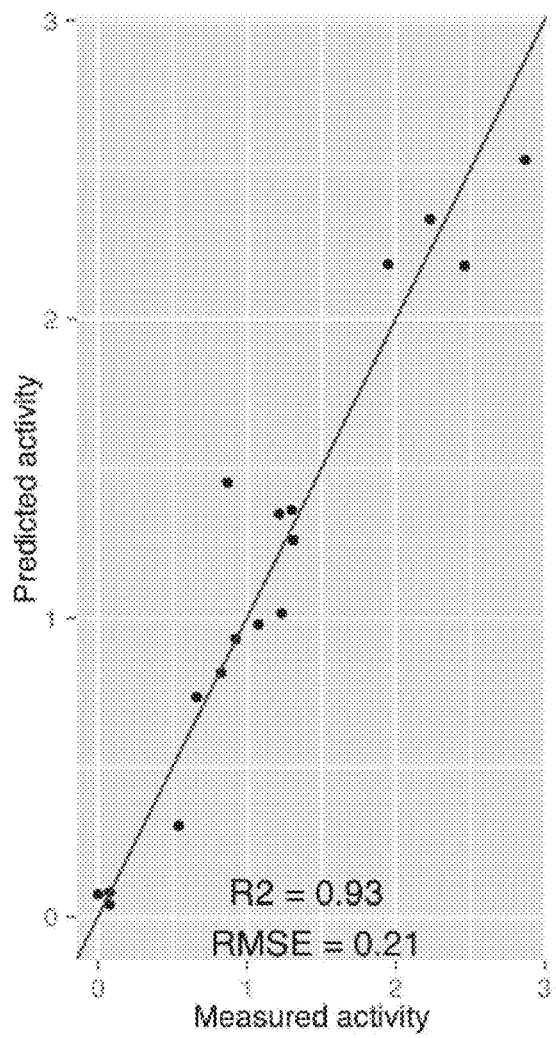
FIGS. 11 and 12 are views similar to that of FIG. 4 with predicted and measured values of the binding affinity, respectively obtained for training and validation subsets of a set of TNF mutants, the training subset being used for computing a database containing protein spectrum values for different values of said binding affinity, and the validation subset being distinct from the training subset and used for testing the relevance of the predicted values.
Figure 12:
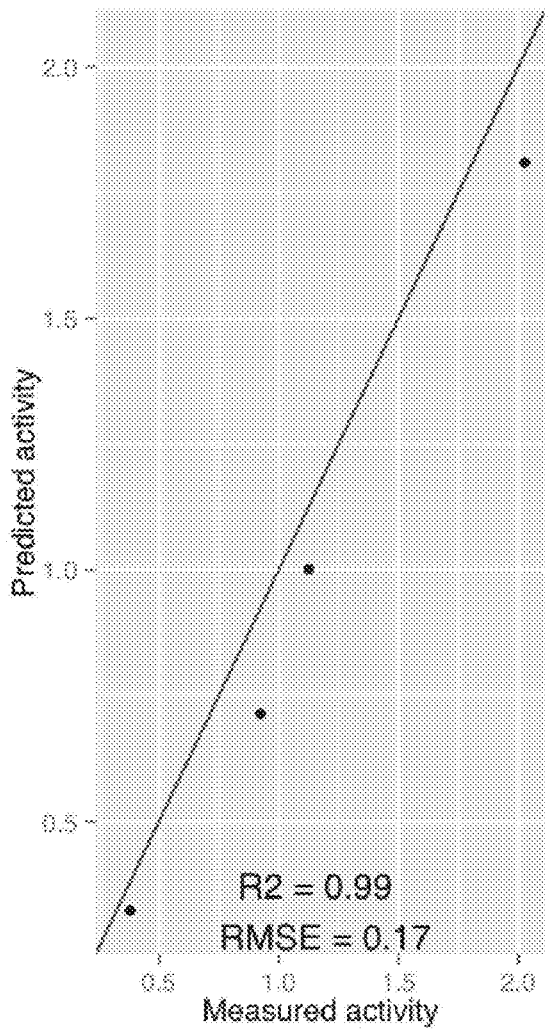
Figure 13:
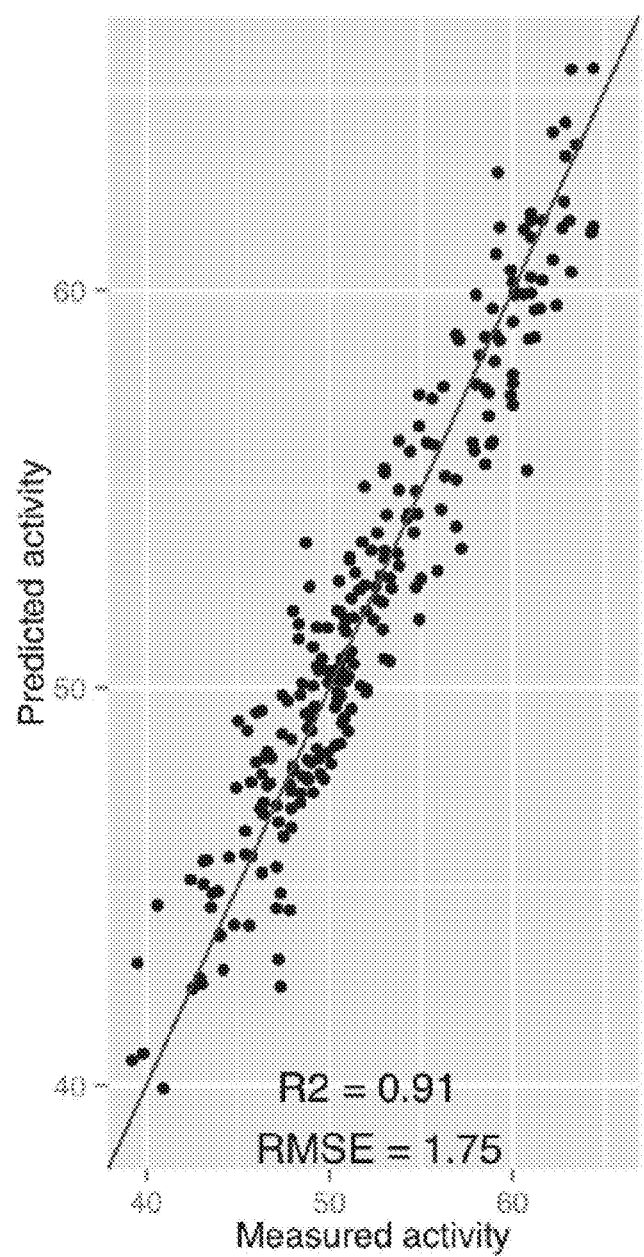
FIG. 13 is a view similar to that of FIG. 4, using a selection of frequency values from the protein spectrum.

Example 5: Mutant TNF with Altered Receptor Selectivity (FIGS. 11 and 12)

In this example, the amino acid sequence of TNF was encoded into a numerical sequence using the following AAindex code: D Weights from the IFH scale (Jacobs and White, Biochemistry. 1989; 28(8):3421-37).

Tumor necrosis factor (TNF) is an important cytokine that suppresses carcinogenesis and excludes infectious pathogens to maintain homeostasis. TNF activates its two receptors, TNF receptor TNFR1 and TNFR2.

Mukai Y et. al. (J Mol Biol. 2009 Jan. 30; 385(4):1221-9) generated receptor-selective TNF mutants that activate only one TNFR.

Receptor selectivity of the 21 mutants disclosed by Mukai et al. (supra) has been predicted using the data mutants (WT+20 mutants including from 1 single mutation to 6 multiple mutations) and data disclosed in this article as learning data set.

TABLE 13

TNF Learning set

| TNF polypeptide | Receptor selectivity |
|---|---|
| WT | 0 |
| K11M, K65S, K90P, K98R, K112N, K128P | 0.079 |
| L29I | 0.079 |
| A84T, V85H, S86K, Q88P, T89Q | 0.544 |
| A84S, V85K, S86T, Q88S, T89H | 0.663 |
| L29Q, R32W | 0.826 |
| L29K, R31A, R32G, E146S, S147T | 0.924 |
| A84S, V85T, S86N, Q88N, T89G | 0.869 |
| A84S, V85S, S86H, Q88R, T89F | 1.079 |
| A84S, V85P, S86L, Q88P, T89K | 1.217 |
| A84T, V85S, S86A, Q88G, T89P | 1.230 |
| A84T, V85T, S86A, Q88S, T89G | 1.310 |
| A145R, E146T, S147D | 1.301 |
| A145K, E146D, S147T | 2.870 |
| A145R, E146E, S147T | 2.228 |
| A145A, E146D, S147D | 1.949 |
| A145A, E146N, S147D | 2.462 |

Competitive binding of TNF to TNFR1 (R1) and TNFR2 (R2) was predicted based on ELISA measurement, as described in the article by Mukai Y et al. Relative affinity (% $K_d$) for R1 and R2 was used to calculate a log R1/R2 ratio. The relative affinity $\log_{10}$(R1/R2) ranges from 0 to 2.87.

In a first step, the method has been applied to the whole dataset. R2 and RMSE are equal to 0.97 and 0.11, respectively, for the binding affinity of TNF. This demonstrates again that this method is able to capture the information linked to the fitness.

In a second step 17 mutants were used as learning sequence and 4 as validation sequences.

TABLE 14

TNF test sequences

| TNF polypeptide | Receptor selectivity |
|---|---|
| L29T_R31G_R32Y | 0.380 |
| L29T_R31K_R32Y | 1.127 |
| L29T_R32F_E146T | 2.026 |
| A84S_V85K_S86T_Q88T_T89H | 0.924 |

Results show that R2 and RMSE are 0.93 and 0.21 respectively for the training set (FIG. 11) and 0.99 and 0.17 for the validation set (FIG. 12) thus indicating that is possible to model the capacity of TNF mutants to bind preferentially with one type of receptor (ratio R1/R2) using the method.

In all the above examples 1 to 5, the whole protein spectrum was used in order to go through prediction. In the following example 6, we demonstrate that the method according to the invention works in a very efficient way using only part of the protein spectrum.

Example 6: Prediction of the Thermostability of Cytochrome P450 Using a Selection of Frequency Values from the Protein Spectrum (FIG. 13)

In this example, the amino acid sequence of cytochrome P450 was encoded into a numerical sequence using the following AAindex code: D Normalized frequency of extended structure (Maxfield and Scheraga, Biochemistry. 1976; 15(23):5138-53)

Here, a selection of the most relevant frequencies coming from the protein spectrum was used to go through prediction. Frequency values are sorted according to their correlation with the fitness, and only the best frequency values are taken into account.

The datasets are the same as in Example 1.

Results show that R2 and RMSE are 0.91 and 1.75 respectively thereby indicating that the fitness, here the thermostability, can be also efficiently predicted with only a part (selection) of frequency from the protein spectrum.

This illustrates that the method of the invention can be used using the whole protein spectrum or part (selection) of frequency from the protein spectrum.

Example 7: Classification of Protein Spectra Using Multivariate Analysis for Protein Screening (FIG. 16)

A subset of Epoxyde hydrolase (as in example 3) including 10 protein spectra with low values and high values of fitness (enantioselectivity) was used. A PCA (Principal Component Analysis) was performed. The low and high values of fitness are in the small oval 180 and large oval 190 respectively, thus indicating that multivariate analysis applied on protein spectra helps for protein screening.

Axes X, Y and Z are the three major components arose from PCA and take into account for 58.28% of the global information related to the collection of protein spectra (respectively: 21.51%, 19.72% and 16.05% in terms of inertia for axes X, Y and Z).

Thus, R2 and RMSE between the predicted values and the measured values of several fitness that were obtained in the aforementioned examples show that the prediction system 20 and method according to the invention allow an efficient prediction of different fitness values of different proteins.

In addition, the method according to the invention allows testing new sequences (validation/test sequences) with mutations or combinations of mutations at other positions that those which were used in the learning sequences set for building the model.

This method also allows testing new sequences (validation/test sequences) with a different number of positions of mutations compared to the number of positions of mutations used in the learning sequences set.

This method also allows testing new sequences including positions of mutations that have not been sampled in the training set. Enterotoxins are given as an example of implementation of the method in such a case.

Further, this method also allows testing new sequences (validation/test sequences) with a different length in terms of number of amino acids compared to the length of the learning sequences set which is used to build a model.

This method enables using the same learning sequences and one or different encoding AAindex and different fitness/activity values as learning data to predict the fitness (validation/test data) for the learning sequences or of the validation sequences: i.e. the ability to predict 2 or more activities/fitness for a protein sequence using this new approach. GLP1 is used as an example in this document: prediction of the Binding affinity to GLP1 Receptor and prediction of the potency using the same AAindex are carried out as an example.

With this method, it is possible to use very small learning sequence and learning data to achieve very good predictions and to obtain mutants with improved fitness. Epoxyde Hydrolase, where only 10 protein sequences were used, is given as an example.

This method furthermore allows using chimeric proteins instead of protein sequences with single point mutations or combinations of single point mutations. Cytochrome P450 is given as an example in this document. Combinations of fragments of different P450 are used.

This invention makes it possible taking into account the effect of interactions between the different AA acids at different positions in an amino acids sequence. FIG. 3 shows that a single point mutation impacts the whole protein spectra, at every frequency.

In addition, this method is very efficient as no more than 10 minutes are necessary after the encoding step for predicting the fitness, while using 50 protein sequences for the learning sequences and 20 protein sequences for the validation sequences.

In addition, the "fitness" of a protein further refers to its adaptation to a criterion, such as protein expression level or mRNA expression level.

Therefore, the "fitness" of a protein refers to its adaptation to a criterion, such as catalytic efficacy, catalytic activity, kinetic constant, Km, Keq, binding affinity, thermostability, solubility, aggregation, potency, toxicity, allergenicity, immunogenicity, thermodynamic stability, flexibility, protein expression level and mRNA expression level. As described above, the "fitness" is also called "activity" and it is considered in the description that the fitness and the activity refer to the same feature.

Fitness such as protein expression level or mRNA expression level will be further illustrated in view of the following examples.

Example 8: Prediction of Protein Expression Level for Bruton's Tyrosine Kinase Variants (FIG. 17)

In this example, the Bruton's Tyrosine Kinase (BTK) is a critical protein involved in the B-cells development and maturation. Indeed, BTK induces antibodies production by the mature B-cells and helps eliminating the infection. Also, a dysfunction of this protein may cause disease like X-linked agammaglobulinemia or Bruton's agammaglobulinemia (B-cells failed to mature).

18 protein variants (Futatani T. et al. 1998, <<*Deficient expression of Bruton's tyrosine kinase in monocytes from X-linked agammaglobulinemia as evaluated by a flow cytometric analysis and its clinical application to carrier detection.*>>, Blood. 1998 Jan. 15; 91(2):595-602; Kanegane H. et al. 2000, <<*Detection of Bruton's tyrosine kinase mutations in hypogammaglobulinaemic males registered as common variable immunodeficiency (CVID) in the Japanese Immunodeficiency Registry*>>, Clin Exp Immunol. 2000 June; 120(3):512-7) and the wild type BTK were used in this example as shown in Table 15 below.

TABLE 15

Sequence and protein expression level values for BTK variants

| Mutations | BTK protein expression level (%) |
|---|---|
| BTK_WT | 100.00 |
| R28P | 4.64 |
| G302Q | 23.92 |
| L358F | 32.99 |
| C502W | 4.69 |
| D521H | 100.21 |
| F644S | 5.98 |
| W124-->Stop | 0.10 |
| Y134-->Stop | 0.31 |
| Q196-->Stop | 0.21 |
| W281-->Stop | 0.93 |
| Y425-->Stop | 0.41 |
| E441-->Stop | 0.10 |
| Q459-->Stop | 0.52 |
| Q497-->Stop | 0.10 |
| W634-->Stop | 0.21 |
| V537E | 10.52 |
| R641H | 6.39 |
| S592T | 0.82 |

Figure 17:
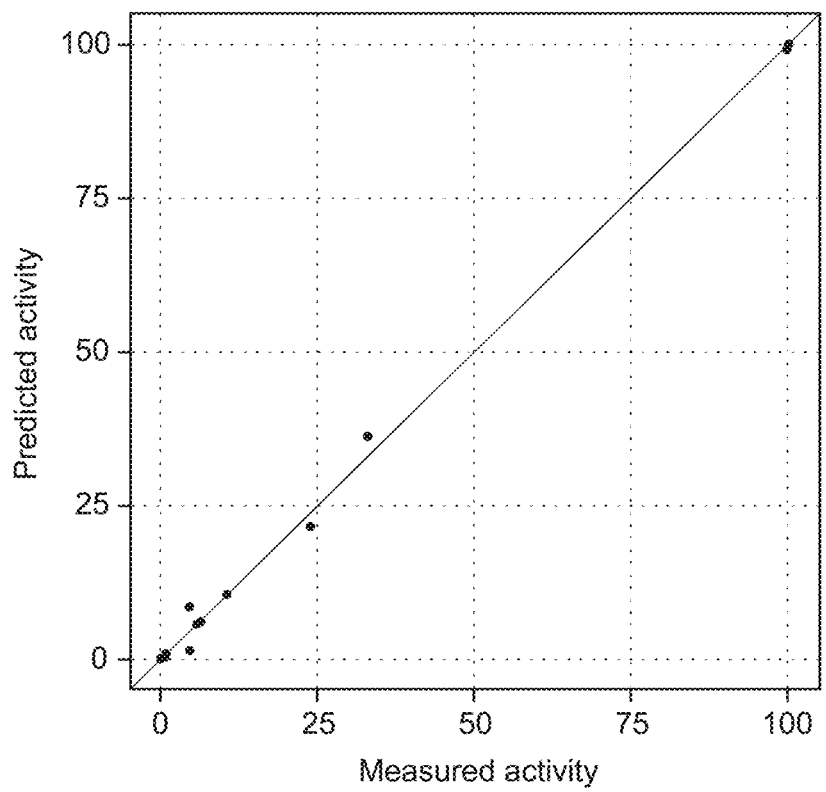
FIG. 17 is a view similar to that of FIG. 4 with predicted and measured values of protein expression levels for Bruton's tyrosine kinase variants.

In FIG. 17, the measured activity corresponds to the in vitro measurements for protein expression level of BTK, and the predicted activity corresponds to the values predicted by the method according to the invention for protein expression level of BTK.

The values are given in percentage of protein expression level with 100% corresponding to the protein expression level of the wild type.

A leave one out cross validation (LOOCV) was used to built the model and to predict the protein expression values. Results show that R2 and RMSE are 0.98 and 1.5 respectively thereby indicating that the fitness, here the protein expression level, can be also efficiently predicted. The protein sequences were encoded using the Optimized relative partition energies—method B (Miyazawa-Jernigan, 1999 Self-consistent estimation of inter-residue protein contact energies based on an equilibrium mixture approximation of residues. *Proteins: Structure, Function, and Bioinformatics*, 34(1), 49-68).

Expression Atlas from EMBL-EBI (http://www.ebi.ac.uk/gxa) provides information about gene and protein expression level in animal and plant samples of different cell types, organism parts, developmental stages, diseases and other conditions. For information about which gene products are present, and at what abundance, in "normal" conditions (e.g. tissue, cell type), the skilled person will refer to Petryszak et al., 2016 <<*Expression Atlas update—an integrated database of gene and protein expression in humans, animals and plants.*>>, Nucl. Acids Res. (4 Jan. 2016) 44 (D1): D746-D752.doi: 10.1093/nar/gkv1045.

Figure 18:
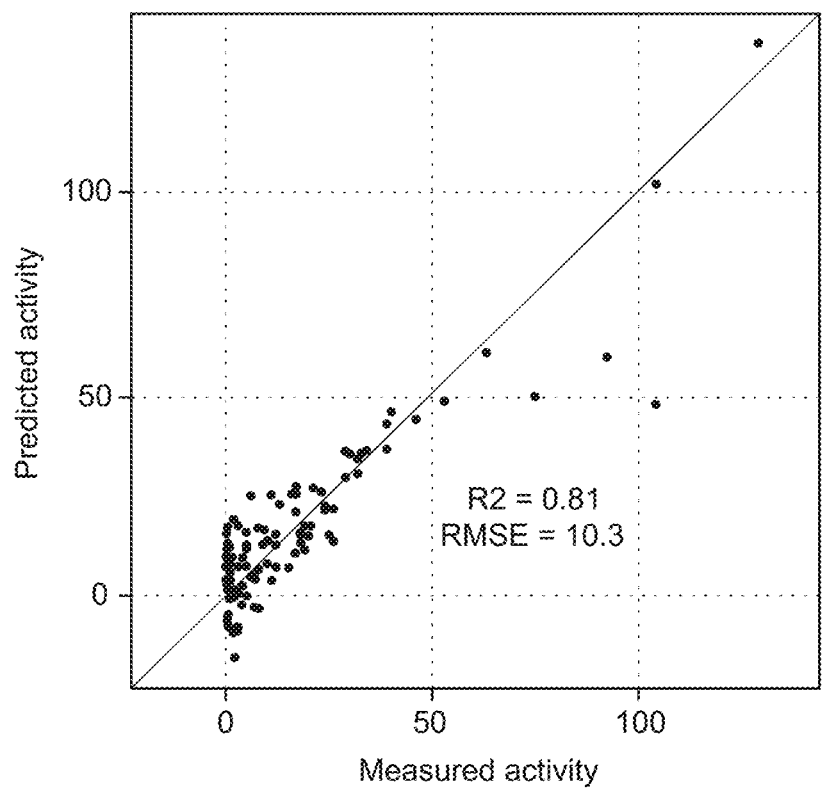
FIG. 18 is a view similar to that of FIG. 4 with predicted and measured values of mRNA expression levels for RNA in the K562 cell line.

Example 9: Prediction of mRNA Expression Level in the K562 Cell Line (FIG. 18)

The method according to the invention is also adapted for predicting mRNA expression level values in K562 Cell line (Fonseca N A et al. 2014 RNA-Seq Gene Profiling—A Systematic Empirical Comparison. PLoS ONE 9(9): e107026. doi:10.1371/journal.pone.0107026). As there is a colinearity between the RNA sequence and the protein sequence, the protein sequence associated with each gene was used in order to build a model. Proteins differ by amino acids composition and length which reflect the RNA sequence and length. The data set (sequences and protein expression levels) are provided in Table 16 below for 97 RNA.

TABLE 16 proteins (as available from Uniprot) and mRNA expression

| K562 PROTEIN | mRNA EXPRESSION |
|---|---|
| >ENSG00000154473_sp_O43684_BUB3_HUMAN_Mitotic_checkpoint_protein_BUB3_OS = Homo_sapiens_GN = BUB3_PE = 1_SV = 1 | 32 |
| >ENSG00000113583_sp_Q8NC54_KCT2_HUMAN_Keratinocyte-associated_transmembrane_protein_2_OS = Homo_sapiens_GN = KCT2_PE = 2_SV = 2 | 29 |
| >ENSG00000108091_sp_Q16204_CCDC6_HUMAN_Coiled-coil_domain-containing_protein_6_OS = Homo_sapiens_GN = CCDC6_PE = 1_SV = 2 | 17 |
| >ENSG00000185559_sp_P80370_DLK1_HUMAN_Protein_delta_homolog_1_OS = Homo_sapiens_GN = DLK1_PE = 1_SV = 3 | 46 |
| >ENSG00000198113_sp_Q9NXH8_TOR4A_HUMAN_Torsin-4A_OS = Homo_sapiens_GN = TOR4A_PE = 1_SV = 2 | 32 |
| >ENSG00000182798_sp_A8MXT2_MAGBH_HUMAN_Melanoma-associated_antigen_B17_OS = Homo_sapiens_GN = MAGEB17_PE = 3_SV = 3 | 0.6 |
| >ENSG00000076513_sp_Q8IZ07_AN13A_HUMAN_Ankyrin_repeat_domain-containing_protein_13A_OS = Homo_sapiens_GN = ANKRD13A_PE = 1_SV = 3 | 17 |
| >ENSG00000130770_sp_Q9UII2_ATIF1_HUMAN_ATPase_inhibitor,_mitochondrial_OS = Homo_sapiens_GN = ATPIF1_PE = 1_SV = 1 | 40 |
| >ENSG00000204052_sp_Q5JTD7_LRC73_HUMAN_Leucine-rich_repeat-containing_protein_73_OS = Homo_sapiens_GN = LRRC73_PE = 2_SV = 1 | 0.3 |
| >ENSG00000183780_sp_Q8IY50_S35F3_HUMAN_Putative_thiamine_transporter_SLC35F3_OS = Homo_sapiens_GN = SLC35F3_PE = 2_SV = 2 | 2 |

TABLE 16-continued proteins (as available from Uniprot) and mRNA expression

| K562 PROTEIN | mRNA EXPRESSION |
|---|---|
| >ENSG00000145002_sp_P0C5J1_F86B2_HUMAN_Putative_protein_N-methyltransferase_FAM86B2_OS = *Homo_sapiens*_GN = FAM86B2_PE = 1_SV = 1 | 0.5 |
| >ENSG00000070770_sp_P19784_CSK22_HUMAN_Casein_kinase_II_subunit_alpha'_OS = *Homo_sapiens*_GN = CSNK2A2_PE = 1_SV = 1 | 30 |
| >ENSG00000144362_sp_Q8TCD6_PHOP2_HUMAN_Pyridoxal_phosphate_phosphatase_PHOSPHO2_OS = *Homo_sapiens*_GN = PHOSPHO2_PE = 1_SV = 1 | 8 |
| >ENSG00000126456_sp_Q14653_IRF3_HUMAN_Interferon_regulatory_factor_3_OS = *Homo_sapiens*_GN = IRF3_PE = 1_SV = 1 | 18 |
| >ENSG00000187475_sp_P22492_H1T_HUMAN_Histone_H1t_OS = *Homo_sapiens*_GN = HIST1H1T_PE = 2_SV = 4 | 1 |
| >ENSG00000173674_sp_P47813_IF1AX_HUMAN_Eukaryotic_translation_initiation_factor_1A,_X-chromosomal_OS = *Homo_sapiens*_GN = EIF1AX_PE = 1_SV = 2 | 53 |
| >ENSG00000131015_sp_Q9BZM5_N2DL2_HUMAN_NKG2D_ligand_2_OS = *Homo_sapiens*_GN = ULBP2_PE = 1_SV = 1 | 9 |
| >ENSG00000177426_sp_Q15583_TGIF1_HUMAN_Homeobox_protein_TGIF1_OS = *Homo_sapiens*_GN = TGIF1_PE = 1_SV = 3 | 8 |
| >ENSG00000181061_sp_Q9Y241_HIG1A_HUMAN_HIG1_domain_family_member_1A,_mitochondrial_OS = *Homo_sapiens*_GN = HIGD1A_PE = 1_SV = 1 | 104 |
| >ENSG00000196119_sp_Q8NGG7_OR8A1_HUMAN_Olfactory_receptor_8A1_OS = *Homo_sapiens*_GN = OR8A1_PE = 2_SV = 2 | 0.3 |
| >ENSG00000111540_sp_P61020_RAB5B_HUMAN_Ras-related_protein_Rab-5B_OS = *Homo_sapiens*_GN = RAB5B_PE = 1_SV = 1 | 19 |
| >ENSG00000142082_sp_Q9NTG7_SIR3_HUMAN_NAD-dependent_protein_deacetylase_sirtuin-3,_mitochondrial_OS = *Homo_sapiens*_GN = SIRT3_PE = 1_SV = 2 | 6 |
| >ENSG00000112273_sp_Q5TGJ6_HDGL1_HUMAN_Hepatoma-derived_growth_factor-like_protein_1_OS = *Homo_sapiens*_GN = HDGFL1_PE = 2_SV = 1 | 0.5 |
| >ENSG00000239521_sp_Q8NAP1_GATS_HUMAN_Putative_protein_GATS_OS = *Homo_sapiens*_GN = GATS_PE = 5_SV = 1 | 2 |
| >ENSG00000165476_sp_Q6NUK4_REEP3_HUMAN_Receptor_expression-enhancing_protein_3_OS = *Homo_sapiens*_GN = REEP3_PE = 1_SV = 1 | 9 |
| >ENSG00000141934_sp_O43688_PLPP2_HUMAN_Phospholipid_phosphatase_2_OS = *Homo_sapiens*_GN = PLPP2_PE = 1_SV = 1 | 0.1 |
| >ENSG00000175854_sp_Q1ZZU3_SWI5_HUMAN_DNA_repair_protein_SWI5_homolog_OS = *Homo_sapiens*_GN = SWI5_PE = 1_SV = 1 | 39 |
| >ENSG00000124194_sp_Q96MZ0_GD1L1_HUMAN_Ganglioside-induced_differentiation-associated_protein_1-like_1_OS = *Homo_sapiens*_GN = GDAP1L1_PE = 2_SV = 2 | 1 |
| >ENSG00000122565_sp_Q13185_CBX3_HUMAN_Chromobox_protein_homolog_3_OS = *Homo_sapiens*_GN = CBX3_PE = 1_SV = 4 | 75 |
| >ENSG00000120053_sp_P17174_AATC_HUMAN_Aspartate_aminotransferase,_cytoplasmic_OS = *Homo_sapiens*_GN = GOT1_PE = 1_SV = 3 | 129 |
| >ENSG00000175793_sp_P31947_1433S_HUMAN_14-3-3_protein_sigma_OS = *Homo_sapiens*_GN = SFN_PE = 1_SV = 1 | 1 |
| >ENSG00000104147_sp_O43482_MS18B_HUMAN_Protein_Mis18-beta_OS = *Homo_sapiens*_GN = OIP5_PE = 1_SV = 2 | 19 |
| >ENSG00000114125_sp_Q9UBF6_RBX2_HUMAN_RING-box_protein_2_OS = *Homo_sapiens*_GN = RNF7_PE = 1_SV = 1 | 25 |
| >ENSG00000153037_sp_P09132_SRP19_HUMAN_Signal_recognition_particle_19_kDa_protein_OS = *Homo_sapiens*_GN = SRP19_PE = 1_SV = 3 | 11 |
| >ENSG00000198939_sp_Q6ZN57_ZFP2_HUMAN_Zinc_finger_protein_2_homolog_OS = *Homo_sapiens*_GN = ZFP2_PE = 1_SV = 1 | 0.2 |
| >ENSG00000061656_sp_Q9NPE6_SPAG4_HUMAN_Sperm-associated_antigen_4_protein_OS = *Homo_sapiens*_GN = SPAG4_PE = 1_SV = 1 | 2 |
| >ENSG00000214575_sp_Q9BZB8_CPEB1_HUMAN_Cytoplasmic_polyadenylation_element-binding_protein_1_OS = *Homo_sapiens*_GN = CPEB1_PE = 1_SV = 1 | 4 |
| >ENSG00000205937_sp_Q15287_RNPS1_HUMAN_RNA-binding_protein_with_serine-rich_domain_1_OS = *Homo_sapiens*_GN = RNPS1_PE = 1_SV = 1 | 23 |
| >ENSG00000256771_sp_O75346_ZN253_HUMAN_Zinc_finger_protein_253_OS = *Homo_sapiens*_GN = ZNF253_PE = 2_SV = 2 | 6 |
| >ENSG00000103037_sp_Q8TBK2_SETD6_HUMAN_N-lysine_methyltransferase_SETD6_OS = *Homo_sapiens*_GN = SETD6_PE = 1_SV = 2 | 3 |
| >ENSG00000064490_sp_O14593_RFXK_HUMAN_DNA-binding_protein_RFXANK_OS = *Homo_sapiens*_GN = RFXANK_PE = 1_SV = 2 | 26 |
| >ENSG00000157800_sp_Q8NCC5_SPX3_HUMAN_Sugar_phosphate_exchanger_3_OS = *Homo_sapiens*_GN = SLC37A3_PE = 2_SV = 2 | 3 |
| >ENSG00000131148_sp_O43402_EMC8_HUMAN_ER_membrane_protein_complex_subunit_8_OS = *Homo_sapiens*_GN = EMC8_PE = 1_SV = 1 | 18 |
| >ENSG00000260428_sp_Q7RTU7_SCX_HUMAN_Basic_helix-loop-helix_transcription_factor_scleraxis_OS = *Homo_sapiens*_GN = SCX_PE = 3_SV = 1 | 0.9 |
| >ENSG00000124508_sp_Q8WVV5_BT2A2_HUMAN_Butyrophilin_subfamily_2_member_A2_OS = *Homo_sapiens*_GN = BTN2A2_PE = 1_SV = 2 | 5 |
| >ENSG00000163040_sp_Q96AQ1_CC74A_HUMAN_Coiled-coil_domain-containing_protein_74A_OS = *Homo_sapiens*_GN = CCDC74A_PE = 2_SV = 1 | 3 |
| >ENSG00000151790_sp_P48775_T23O_HUMAN_Tryptophan_2,3-dioxygenase_OS = *Homo_sapiens*_GN = TDO2_PE = 1_SV = 1 | 0.7 |
| >ENSG00000040608_sp_Q9BZR6_RTN4R_HUMAN_Reticulon-4_receptor_OS = *Homo_sapiens*_GN = RTN4R_PE = 1_SV = 1 | 0.6 |
| >ENSG00000102931_sp_Q9Y2Y0_AR2BP_HUMAN_ADP-ribosylation_factor-like_protein_2-binding_protein_OS = *Homo_sapiens*_GN = ARL2BP_PE = 1_SV = 1 | 7 |

TABLE 16-continued proteins (as available from Uniprot) and mRNA expression

| K562 PROTEIN | mRNA EX-PRES-SION |
|---|---|
| >ENSG00000125037_sp_Q9P0I2_EMC3_HUMAN_ER_membrane_protein_complex_subunit_3_OS = Homo_sapiens_ GN = EMC3_PE = 1_SV = 3 | 29 |
| >ENSG00000147416_sp_P21281_VATB2_HUMAN_V-type_proton_ATPase_subunit_B,_brain_isoform_OS = Homo_sapiens_GN = ATP6V1B2_PE = 1_SV = 3 | 33 |
| >ENSG00000070718_sp_P53677_AP3M2_HUMAN_AP-3_complex_subunit_mu-2_OS = Homo_sapiens_GN = AP3M2_PE = 2_SV = 1 | 8 |
| >ENSG00000172354_sp_P62879_GBB2_HUMAN_Guanine_nucleotide-binding_protein_G(I)/G(S)/G(T)_subunit_beta-2_OS = Homo_sapiens_GN = GNB2_PE = 1_SV = 3 | 104 |
| >ENSG00000153498_sp_Q96KW9_SPAC7_HUMAN_Sperm_acrosome-associated_protein_7_OS = Homo_sapiens_GN = SPACA7_PE = 1_SV = 2 | 0.1 |
| >ENSG00000188610_sp_Q86X60_FA72B_HUMAN_Protein_FAM72B_OS = Homo_sapiens_GN = FAM72B_PE = 2_SV = 2 | 7 |
| >ENSG00000010072_sp_Q9H040_SPRTN_HUMAN_SprT-like_domain-containing_protein_Spartan_OS = Homo_sapiens_GN = SPRTN_PE = 1_SV = 2 | 7 |
| >ENSG00000103121_sp_Q9NRP2_COXM2_HUMAN_COX_assembly_mitochondrial_protein_2_homolog_OS = Homo_sapiens_GN = CMC2_PE = 1_SV = 1 | 5 |
| >ENSG00000128654_sp_O75431_MTX2_HUMAN_Metaxin-2_OS = Homo_sapiens_GN = MTX2_PE = 1_SV = 1 | 63 |
| >ENSG00000169359_sp_O00400_ACATN_HUMAN_Acetyl-coenzyme_A_transporter_1_OS = Homo_sapiens_GN = SLC33A1_PE = 1_SV = 1 | 11 |
| >ENSG00000181885_sp_O95471_CLD7_HUMAN_Claudin-7_OS = Homo_sapiens_GN = CLDN7_PE = 1_SV = 4 | 4 |
| >ENSG00000102078_sp_O95258_UCP5_HUMAN_Brain_mitochondrial_carrier_protein_1_OS = Homo_sapiens_GN = SLC25A14_PE = 2_SV = 1 | 5 |
| >ENSG00000177854_sp_Q14656_TM187_HUMAN_Transmembrane_protein_187_OS = Homo_sapiens_GN = TMEM187_ PE = 2_SV = 1 | 3 |
| >ENSG00000073792_sp_Q9Y6M1_IF2B2_HUMAN_Insulin-like_growth_factor_2_mRNA-binding_protein_2_OS = Homo_sapiens_GN = IGF2BP2_PE = 1_SV = 2 | 24 |
| >ENSG00000197849_sp_Q15617_OR8G1_HUMAN_Olfactory_receptor_8G1_OS = Homo_sapiens_GN = OR8G1_PE = 2_ SV = 2 | 0.3 |
| >ENSG00000152076_sp_Q96LY2_CC74B_HUMAN_Coiled-coil_domain-containing_protein_74B_OS = Homo_sapiens_GN = CCDC74B_PE = 2_SV = 1 | 0.3 |
| >ENSG00000173272_sp_Q6P582_MZT2A_HUMAN_Mitotic-spindle_organizing_protein_2A_OS = Homo_sapiens_GN = MZT2A_PE = 1_SV = 2 | 15 |
| >ENSG00000166289_sp_Q96S99_PKHF1_HUMAN_Pleckstrin_homology_domain-containing_family_F_member_1_OS = Homo_sapiens_GN = PLEKHF1_PE = 1_SV = 3 | 21 |
| >ENSG00000172466_sp_P17028_ZNF24_HUMAN_Zinc_finger_protein_24_OS = Homo_sapiens_GN = ZNF24_PE = 1_SV = 4 | 34 |
| >ENSG00000188811_sp_Q5JS37_NHLC3_HUMAN_NHL_repeat-containing_protein_3_OS = Homo_sapiens_GN = NHLRC3_PE = 2_SV = 1 | 4 |
| >ENSG00000119715_sp_O95718_ERR2_HUMAN_Steroid_hormone_receptor_ERR2_OS = Homo_sapiens_GN = ESRRB_ PE = 1_SV = 2 | 13 |
| >ENSG00000148950_sp_Q96LU5_IMP1L_HUMAN_Mitochondrial_inner_membrane_protease_subunit_1_OS = Homo_ sapiens_GN = IMMP1L_PE = 2_SV = 1 | 12 |
| >ENSG00000186197_sp_Q8WWZ3_EDAD_HUMAN_Ectodysplasin-A_receptor-associated_adapter_protein_OS = Homo_sapiens_GN = EDARADD_PE = 1_SV = 3 | 5 |
| >ENSG00000182287_sp_P56377_AP1S2_HUMAN_AP-1_complex_subunit_sigma-2_OS = Homo_sapiens_GN = AP1S2_PE = 1_SV = 1 | 26 |
| >ENSG00000132475_sp_P84243_H33_HUMAN_Histone_H3.3_OS = Homo_sapiens_GN = H3F3A_PE = 1_SV = 2 | 92 |
| >ENSG00000185899_sp_P59551_T2R60_HUMAN_Taste_receptor_type_2_member_60_OS = Homo_sapiens_GN = TAS2R60_PE = 2_SV = 1 | 0.4 |
| >ENSG00000095261_sp_Q16401_PSMD5_HUMAN_26S_proteasome_non-ATPase_regulatory_subunit_5_OS = Homo_sapiens_GN = PSMD5_PE = 1_SV = 3 | 39 |
| >ENSG00000268940_sp_Q5HYN5_CT451_HUMAN_Cancer/testis_antigen_family_45_member_A1_OS = Homo_sapiens_ GN = CT45A1_PE = 2_SV = 1 | 0.3 |
| >ENSG00000176485_sp_P53816_HRSL3_HUMAN_HRAS-like_suppressor_3_OS = Homo_sapiens_GN = PLA2G16_PE = 1_SV = 2 | 3 |
| >ENSG00000163900_sp_Q96HV5_TM41A_HUMAN_Transmembrane_protein_41A_OS = Homo_sapiens_GN = TMEM41A_ PE = 1_SV = 1 | 10 |
| >ENSG00000145777_sp_Q969D9_TSLP_HUMAN_Thymic_stromal_lymphopoietin_OS = Homo_sapiens_GN = TSLP_PE = 1_SV = 1 | 2 |
| >ENSG00000087088_sp_Q07812_BAX_HUMAN_Apoptosis_regulator_BAX_OS = Homo_sapiens_GN = BAX_PE = 1_SV = 1 | 24 |
| >ENSG00000163001_sp_Q96G28_CFA36_HUMAN_Cilia-_and_flagella-associated_protein_36_OS = Homo_sapiens_GN = CFAP36_PE = 1_SV = 2 | 10 |
| >ENSG00000241127_sp_Q9NRH1_YAED1_HUMAN_Yae1_domain-containing_protein_1_OS = Homo_sapiens_GN = YAE1D1_PE = 2_SV = 1 | 5 |
| >ENSG00000176407_sp_Q9P0J7_KCMF1_HUMAN_E3_ubiquitin-protein_ligase_KCMF1_OS = Homo_sapiens_GN = KCMF1_PE = 1_SV = 2 | 18 |
| >ENSG00000111291_sp_Q9NZD1_GPC5D_HUMAN_G-protein_coupled_receptor_family_C_group_5_member_D_OS = Homo_sapiens_GN = GPRC5D_PE = 2_SV = 1 | 0.3 |
| >ENSG00000113240_sp_Q9HAZ1_CLK4_HUMAN_Dual_specificity_protein_kinase_CLK4_OS = Homo_sapiens_GN = CLK4_PE = 1_SV = 1 | 2 |
| >ENSG00000157778_sp_Q9BT73_PSMG3_HUMAN_Proteasome_assembly_chaperone_3_OS = Homo_sapiens_GN = PSMG3_PE = 1_SV = 1 | 17 |

TABLE 16-continued proteins (as available from Uniprot) and mRNA expression

| K562 PROTEIN | mRNA EXPRESSION |
|---|---|
| >ENSG00000140043_sp_Q8N8N7_PTGR2_HUMAN_Prostaglandin_reductase_2_OS = Homo_sapiens_GN = PTGR2_PE = 1_SV = 1 | 2 |
| >ENSG00000163257_sp_Q9NXF7_DCA16_HUMAN_DDB1-_and_CUL4-associated_factor_16_OS = Homo_sapiens_GN = DCAF16_PE = 1_SV = 1 | 16 |
| >ENSG00000165406_sp_Q5T0T0_MARH8_HUMAN_E3_ubiquitin-protein_ligase_MARCH8_OS = Homo_sapiens_GN = MARCH8_PE = 1_SV = 1 | 20 |
| >ENSG00000224659_sp_A6NER3_GG12J_HUMAN_G_antigen_12J_OS = Homo_sapiens_GN = GAGE12J_PE = 3_SV = 1 | 0.5 |
| >ENSG00000163812_sp_Q9NYG2_ZDHC3_HUMAN_Palmitoyltransferase_ZDHHC3_OS = Homo_sapiens_GN = ZDHHC3_PE = 1_SV = 2 | 12 |
| >ENSG00000079332_sp_Q9NR31_SAR1A_HUMAN_GTP-binding_protein_SAR1a_OS = Homo_sapiens_GN = SAR1A_PE = 1_SV = 1 | 17 |
| >ENSG00000184154_sp_Q8WZ04_TOMT_HUMAN_Transmembrane_O-methyltransferase_OS = Homo_sapiens_GN = LRTOMT_PE = 1_SV = 3 | 1 |
| >ENSG00000138303_sp_Q8N9N2_ASCC1_HUMAN_Activating_signal_cointegrator_1_complex_subunit_1_OS = Homo_sapiens_GN = ASCC1_PE = 1_SV = 1 | 12 |
| >ENSG00000171227_sp_Q8WXS4_CCGL_HUMAN_Voltage-dependent_calcium_channel_gamma-like_subunit_OS = Homo_sapiens_GN = TMEM37_PE = 2_SV = 2 | 1 |
| >ENSG00000107164_sp_Q96I24_FUBP3_HUMAN_Far_upstream_element-binding_protein_3_OS = Homo_sapiens_GN = FUBP3_PE = 1_SV = 2 | 20 |

FIG. 18 shows the results obtained using a leave one out cross validation (R2: 0.81, RMSE: 10.3), thereby illustrating that the method according to the invention is also adapted for predicting mRNA expression level through the protein sequence associated with RNA.

The protein sequences were encoded using the Hydropathy scale based on self-information values in the two-state model (25% accessibility) (Naderi-Manesh et al., 2001 Prediction of protein surface accessibility with information theory. *Proteins: Structure, Function, and Bioinformatics*, 42(4), 452-459).

Figure 19:
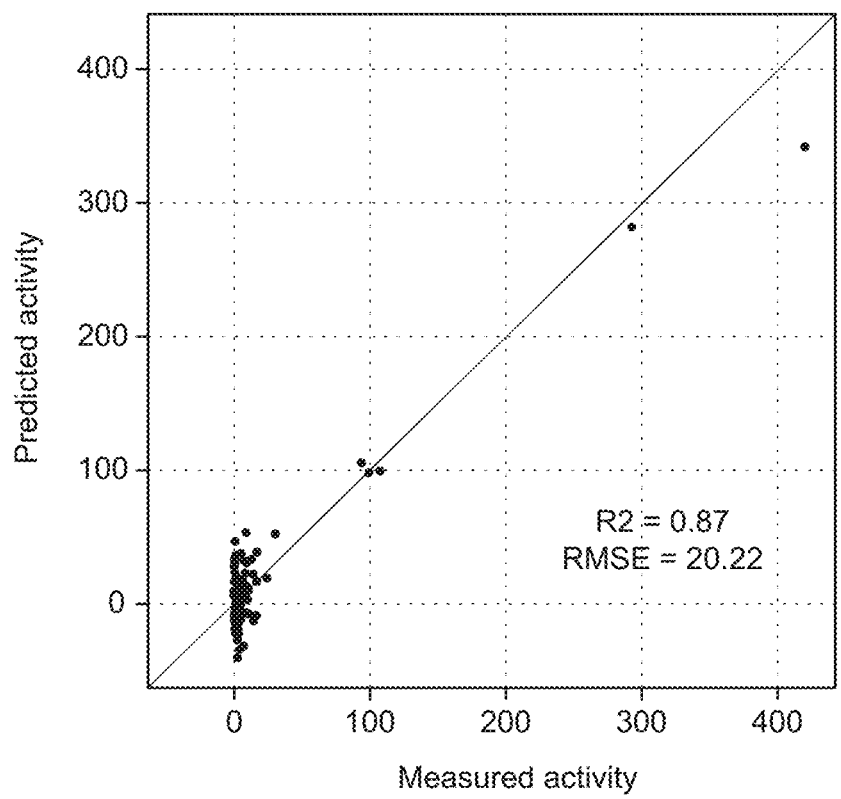
FIG. 19 is a view similar to that of FIG. 4 with predicted and measured values of protein expression levels for proteins in heart cell.

Example 10: Prediction of Protein Expression Level of Different Proteins in Heart Cell (FIG. 19)

The method according to the invention was also used to predict protein expression level values of different proteins in heart cell. Proteins differ by amino acids composition and length. The data set (sequences and protein expression levels) are provided in Table 17 below for 85 proteins.

TABLE 17 heart proteins (as available from Uniprot) and protein expression

| HEART PROTEIN | PROTEIN EXPRESSION |
|---|---|
| >ENSG00000004779_sp_O14561_ACPM_HUMAN_Acyl_carrier_protein,_mitochondrial_OS = Homo_sapiens_GN = NDUFAB1_PE = 1_SV = 3 | 3.694 |
| >ENSG00000060762_sp_Q9Y5U8_MPC1_HUMAN_Mitochondrial_pyruvate_carrier_1_OS = Homo_sapiens_GN = MPC1_PE = 1_SV = 1 | 3.38 |
| >ENSG00000065518_sp_O95168_NDUB4_HUMAN_NADH_dehydrogenase_[ubiquinone]_1_beta_subcomplex_subunit_4_OS = Homo_sapiens_GN = NDUFB4_PE = 1_SV = 3 | 3.813 |
| >ENSG00000090263_sp_Q9Y291_RT33_HUMAN_28S_ribosomal_protein_S33,_mitochondrial_OS = Homo_sapiens_GN = MRPS33_PE = 1_SV = 1 | 0.091 |
| >ENSG00000091482_sp_Q9UHP9_SMPX_HUMAN_Small_muscular_protein_OS = Homo_sapiens_GN = SMPX_PE = 2_SV = 3 | 1.312 |
| >ENSG00000099624_sp_P30049_ATPD_HUMAN_ATP_synthase_subunit_delta,_mitochondrial_OS = Homo_sapiens_GN = ATP5D_PE = 1_SV = 2 | 14.198 |
| >ENSG00000099795_sp_P17568_NDUB7_HUMAN_NADH_dehydrogenase_[ubiquinone]_1_beta_subcomplex_subunit_7_OS = Homo_sapiens_GN = NDUFB7_PE = 1_SV = 4 | 2.417 |
| >ENSG00000106631_sp_Q01449_MLRA_HUMAN_Myosin_regulatory_light_chain_2,_atrial_isoform_OS = Homo_sapiens_GN = MYL7_PE = 1_SV = 1 | 0.236 |
| >ENSG00000106992_sp_P00568_KAD1_HUMAN_Adenylate_kinase_isoenzyme_1_OS = Homo_sapiens_GN = AK1_PE = 1_SV = 3 | 9.035 |
| >ENSG00000107020_sp_Q9HBL7_PLRKT_HUMAN_Plasminogen_receptor_(KT)_OS = Homo_sapiens_GN = PLGRKT_PE = 1_SV = 1 | 0.669 |
| >ENSG00000109846_sp_P02511_CRYAB_HUMAN_Alpha-crystallin_B_chain_OS = Homo_sapiens_GN = CRYAB_PE = 1_SV = 2 | 98.769 |
| >ENSG00000111245_sp_P10916_MLRV_HUMAN_Myosin_regulatory_light_chain_2,_ventricular/cardiac_muscle_isoform_OS = Homo_sapiens_GN = MYL2_PE = 1_SV = 3 | 93.624 |
| >ENSG00000111843_sp_Q9P0S9_TM14C_HUMAN_Transmembrane_protein_14C_OS = Homo_sapiens_GN = TMEM14C_PE = 1_SV = 1 | 1.047 |

TABLE 17-continued heart proteins (as available from Uniprot) and protein expression

| HEART PROTEIN | PROTEIN EXPRESSION |
|---|---|
| >ENSG00000114023_sp_Q96A26_F162A_HUMAN_Protein_FAM162A_OS = Homo_sapiens_GN = FAM162A_PE = 1_SV = 2 | 1.891 |
| >ENSG00000114854_sp_P63316_TNNC1_HUMAN_Troponin_C,_slow_skeletal_and_cardiac_muscles_OS = Homo_sapiens_GN = TNNC1_PE = 1_SV = 1 | 16.369 |
| >ENSG00000115204_sp_P39210_MPV17_HUMAN_Protein_Mpv17_OS = Homo_sapiens_GN = MPV17_PE = 1_SV = 1 | 0.741 |
| >ENSG00000119013_sp_O43676_NDUB3_HUMAN_NADH_dehydrogenase_[ubiquinone]_1_beta_subcomplex_subunit_3_OS = Homo_sapiens_GN = NDUFB3_PE = 1_SV = 3 | 2.354 |
| >ENSG00000119421_sp_P51970_NDUA8_HUMAN_NADH_dehydrogenase_[ubiquinone]_1_alpha_subcomplex_subunit_8_OS = Homo_sapiens_GN = NDUFA8_PE = 1_SV = 3 | 4.214 |
| >ENSG00000121769_sp_P05413_FABPH_HUMAN_Fatty_acid-binding_protein,_heart_OS = Homo_sapiens_GN = FABP3_PE = 1_SV = 4 | 106.504 |
| >ENSG00000126267_sp_P14854_CX6B1_HUMAN_Cytochrome_c_oxidase_subunit_6B1_OS = Homo_sapiens_GN = COX6B1_PE = 1_SV = 2 | 8.167 |
| >ENSG00000127184_sp_P15954_COX7C_HUMAN_Cytochrome_c_oxidase_subunit_7C,_mitochondrial_OS = Homo_sapiens_GN = COX7C_PE = 1_SV = 1 | 2.376 |
| >ENSG00000128609_sp_Q16718_NDUA5_HUMAN_NADH_dehydrogenase_[ubiquinone]_1_alpha_subcomplex_subunit_5_OS = Homo_sapiens_GN = NDUFA5_PE = 1_SV = 1 | 7.363 |
| >ENSG00000128626_sp_O15235_RT12_HUMAN_28S_ribosomal_protein_S12,_mitochondrial_OS = Homo_sapiens_GN = MRPS12_PE = 1_SV = 1 | 0.247 |
| >ENSG00000129170_sp_P50461_CSRP3_HUMAN_Cysteine_and_glycine-rich_protein_3_OS = Homo_sapiens_GN = CSRP3_PE = 1_SV = 1 | 14.235 |
| >ENSG00000131143_sp_P13073_COX41_HUMAN_Cytochrome_c_oxidase_subunit_4_isoform_1,_mitochondrial_OS = Homo_sapiens_GN = COX4I1_PE = 1_SV = 1 | 29.782 |
| >ENSG00000131368_sp_P82663_RT25_HUMAN_28S_ribosomal_protein_S25,_mitochondrial_OS = Homo_sapiens_GN = MRPS25_PE = 1_SV = 1 | 0.299 |
| >ENSG00000131495_sp_O43678_NDUA2_HUMAN_NADH_dehydrogenase_[ubiquinone]_1_alpha_subcomplex_subunit_2_OS = Homo_sapiens_GN = NDUFA2_PE = 1_SV = 3 | 2.156 |
| >ENSG00000135940_sp_P10606_COX5B_HUMAN_Cytochrome_c_oxidase_subunit_5B,_mitochondrial_OS = Homo_sapiens_GN = COX5B_PE = 1_SV = 2 | 11.056 |
| >ENSG00000136521_sp_O43674_NDUB5_HUMAN_NADH_dehydrogenase_[ubiquinone]_1_beta_subcomplex_subunit_5,_mitochondrial_OS = Homo_sapiens_GN = NDUFB5_PE = 1_SV = 1 | 2.353 |
| >ENSG00000137168_sp_Q9Y3C6_PPIL1_HUMAN_Peptidyl-prolyl_cis-trans_isomerase-like_1_OS = Homo_sapiens_GN = PPIL1_PE = 1_SV = 1 | 1.533 |
| >ENSG00000138495_sp_Q14061_COX17_HUMAN_Cytochrome_c_oxidase_copper_chaperone_OS = Homo_sapiens_GN = COX17_PE = 1_SV = 2 | 1.158 |
| >ENSG00000140990_sp_O96000_NDUBA_HUMAN_NADH_dehydrogenase_[ubiquinone]_1_beta_subcomplex_subunit_10_OS = Homo_sapiens_GN = NDUFB10_PE = 1_SV = 3 | 3.275 |
| >ENSG00000143198_sp_O14880_MGST3_HUMAN_Microsomal_glutathione_S-transferase_3_OS = Homo_sapiens_GN = MGST3_PE = 1_SV = 1 | 10.296 |
| >ENSG00000143252_sp_Q99643_C560_HUMAN_Succinate_dehydrogenase_cytochrome_b560_subunit,_mitochondrial_OS = Homo_sapiens_GN = SDHC_PE = 1_SV = 1 | 5.157 |
| >ENSG00000145494_sp_O75380_NDUS6_HUMAN_NADH_dehydrogenase_[ubiquinone]_iron-sulfur_protein_6,_mitochondrial_OS = Homo_sapiens_GN = NDUFS6_PE = 1_SV = 1 | 4.148 |
| >ENSG00000147123_sp_Q9NX14_NDUBB_HUMAN_NADH_dehydrogenase_[ubiquinone]_1_beta_subcomplex_subunit_11,_mitochondrial_OS = Homo_sapiens_GN = NDUFB11_PE = 1_SV = 1 | 2.429 |
| >ENSG00000147586_sp_Q9Y2Q9_RT28_HUMAN_28S_ribosomal_protein_S28,_mitochondrial_OS = Homo_sapiens_GN = MRPS28_PE = 1_SV = 1 | 0.253 |
| >ENSG00000147684_sp_Q9Y6M9_NDUB9_HUMAN_NADH_dehydrogenase_[ubiquinone]_1_beta_subcomplex_subunit_9_OS = Homo_sapiens_GN = NDUFB9_PE = 1_SV = 3 | 5.076 |
| >ENSG00000148450_sp_Q9Y3D2_MSRB2_HUMAN_Methionine-R-sulfoxide_reductase_B2,_mitochondrial_OS = Homo_sapiens_GN = MSRB2_PE = 1_SV = 2 | 0.271 |
| >ENSG00000151366_sp_O95298_NDUC2_HUMAN_NADH_dehydrogenase_[ubiquinone]_1_subunit_C2_OS = Homo_sapiens_GN = NDUFC2_PE = 1_SV = 1 | 5.998 |
| >ENSG00000152137_sp_Q9UJY1_HSPB8_HUMAN_Heat_shock_protein_beta-8_OS = Homo_sapiens_GN = HSPB8_PE = 1_SV = 1 | 1.168 |
| >ENSG00000156411_sp_P56378_68MP_HUMAN_6.8_kDa_mitochondrial_proteolipid_OS = Homo_sapiens_GN = MP68_PE = 1_SV = 1 | 7.5 |
| >ENSG00000156467_sp_P14927_QCR7_HUMAN_Cytochrome_b-c1_complex_subunit_7_OS = Homo_sapiens_GN = UQCRB_PE = 1_SV = 2 | 4.168 |
| >ENSG00000160124_sp_Q4VC31_CCD58_HUMAN_Coiled-coil_domain-containing_protein_58_OS = Homo_sapiens_GN = CCDC58_PE = 1_SV = 1 | 0.712 |
| >ENSG00000160678_sp_P23297_S10A1_HUMAN_Protein_S100-A1_OS = Homo_sapiens_GN = S100A1_PE = 1_SV = 2 | 16.819 |
| >ENSG00000160808_sp_P08590_MYL3_HUMAN_Myosin_light_chain_3_OS = Homo_sapiens_GN = MYL3_PE = 1_SV = 3 | 290.72 |
| >ENSG00000161281_sp_P24310_CX7A1_HUMAN_Cytochrome_c_oxidase_subunit_7A1,_mitochondrial_OS = Homo_sapiens_GN = COX7A1_PE = 1_SV = 2 | 3.707 |
| >ENSG00000164258_sp_O43181_NDUS4_HUMAN_NADH_dehydrogenase_[ubiquinone]_iron-sulfur_protein_4,_mitochondrial_OS = Homo_sapiens_GN = NDUFS4_PE = 1_SV = 1 | 3.613 |
| >ENSG00000164405_sp_O14949_QCR8_HUMAN_Cytochrome_b-c1_complex_subunit_8_OS = Homo_sapiens_GN = UQCRQ_PE = 1_SV = 4 | 5.88 |
| >ENSG00000164898_sp_Q96HJ9_CG055_HUMAN_UPF0562_protein_C7orf55_OS = Homo_sapiens_GN = C7orf55_PE = 1_SV = 2 | 0.846 |

TABLE 17-continued heart proteins (as available from Uniprot) and protein expression

| HEART PROTEIN | PROTEIN EXPRESSION |
|---|---|
| >ENSG00000164919_sp_P09669_COX6C_HUMAN_Cytochrome_c_oxidase_subunit_6C_OS = Homo_sapiens_GN = COX6C_PE = 1_SV = 2 | 11.002 |
| >ENSG00000165264_sp_O95139_NDUB6_HUMAN_NADH_dehydrogenase_[ubiquinone]_1_beta_subcomplex_subunit_6_OS = Homo_sapiens_GN = NDUFB6_PE = 1_SV = 3 | 2.055 |
| >ENSG00000165775_sp_Q9BWH2_FUND2_HUMAN_FUN14_domain-containing_protein_2_OS = Homo_sapiens_GN = FUNDC2_PE = 1_SV = 2 | 1.988 |
| >ENSG00000167283_sp_O75964_ATP5L_HUMAN_ATP_synthase_subunit_g,_mitochondrial_OS = Homo_sapiens_GN = ATP5L_PE = 1_SV = 3 | 12.652 |
| >ENSG00000167863_sp_O75947_ATP5H_HUMAN_ATP_synthase_subunit_d,_mitochondrial_OS = Homo_sapiens_GN = ATP5H_PE = 1_SV = 3 | 9.278 |
| >ENSG00000168653_sp_O43920_NDUS5_HUMAN_NADH_dehydrogenase_[ubiquinone]_iron-sulfur_protein_5_OS = Homo_sapiens_GN = NDUFS5_PE = 1_SV = 3 | 3.315 |
| >ENSG00000169020_sp_P56385_ATP5I_HUMAN_ATP_synthase_subunit_e,_mitochondrial_OS = Homo_sapiens_GN = ATP5I_PE = 1_SV = 2 | 8.737 |
| >ENSG00000169271_sp_Q12988_HSPB3_HUMAN_Heat_shock_protein_beta-3_OS = Homo_sapiens_GN = HSPB3_PE = 1_SV = 2 | 0.506 |
| >ENSG00000170906_sp_O95167_NDUA3_HUMAN_NADH_dehydrogenase_[ubiquinone]_1_alpha_subcomplex_subunit_3_OS = Homo_sapiens_GN = NDUFA3_PE = 1_SV = 1 | 1.709 |
| >ENSG00000171202_sp_Q9H061_T126A_HUMAN_Transmembrane_protein_126A_OS = Homo_sapiens_GN = TMEM126A_PE = 1_SV = 1 | 0.93 |
| >ENSG00000172115_sp_P99999_CYC_HUMAN_Cytochrome_c_OS = Homo_sapiens_GN = CYCS_PE = 1_SV = 2 | 24.738 |
| >ENSG00000173641_sp_Q9UBY9_HSPB7_HUMAN_Heat_shock_protein_beta-7_OS = Homo_sapiens_GN = HSPB7_PE = 1_SV = 1 | 3.446 |
| >ENSG00000173915_sp_Q96IX5_USMG5_HUMAN_Up-regulated_during_skeletal_muscle_growth_protein_5_OS = Homo_sapiens_GN = USMG5_PE = 1_SV = 1 | 6.522 |
| >ENSG00000173991_sp_O15273_TELT_HUMAN_Telethonin_OS = Homo_sapiens_GN = TCAP_PE = 1_SV = 1 | 1.561 |
| >ENSG00000174886_sp_Q86Y39_NDUAB_HUMAN_NADH_dehydrogenase_[ubiquinone]_1_alpha_subcomplex_subunit_11_OS = Homo_sapiens_GN = NDUFA11_PE = 1_SV = 3 | 3.187 |
| >ENSG00000174917_sp_Q5XKP0_MIC13_HUMAN_MICOS_complex_subunit_MIC13_OS = Homo_sapiens_GN = MIC13_PE = 1_SV = 1 | 0.707 |
| >ENSG00000176171_sp_Q12983_BNIP3_HUMAN_BCL2/adenovirus_E1B_19_kDa_protein-interacting_protein_3_OS = Homo_sapiens_GN = BNIP3_PE = 1_SV = 2 | 0.13 |
| >ENSG00000178057_sp_Q9BU61_NDUF3_HUMAN_NADH_dehydrogenase_[ubiquinone]_1_alpha_subcomplex_assembly_factor_3_OS = Homo_sapiens_GN = NDUFAF3_PE = 1_SV = 1 | 0.404 |
| >ENSG00000178741_sp_P20674_COX5A_HUMAN_Cytochrome_c_oxidase_subunit_5A,_mitochondrial_OS = Homo_sapiens_GN = COX5A_PE = 1_SV = 2 | 9.505 |
| >ENSG00000181061_sp_Q9Y241_HIG1A_HUMAN_HIG1_domain_family_member_1A,_mitochondrial_OS = Homo_sapiens_GN = HIGD1A_PE = 1_SV = 1 | 1.196 |
| >ENSG00000181991_sp_P82912_RT11_HUMAN_28S_ribosomal_protein_S11,_mitochondrial_OS = Homo_sapiens_GN = MRPS11_PE = 1_SV = 2 | 0.219 |
| >ENSG00000183648_sp_O75438_NDUB1_HUMAN_NADH_dehydrogenase_[ubiquinone]_1_beta_subcomplex_subunit_1_OS = Homo_sapiens_GN = NDUFB1_PE = 1_SV = 1 | 0.825 |
| >ENSG00000183978_sp_Q9Y2R0_COA3_HUMAN_Cytochrome_c_oxidase_assembly_factor_3_homolog,_mitochondrial_OS = Homo_sapiens_GN = COA3_PE = 1_SV = 1 | 0.959 |
| >ENSG00000184076_sp_Q9UDW1_QCR9_HUMAN_Cytochrome_b-c1_complex_subunit_9_OS = Homo_sapiens_GN = UQCR10_PE = 1_SV = 3 | 5.379 |
| >ENSG00000184752_sp_Q9UI09_NDUAC_HUMAN_NADH_dehydrogenase_[ubiquinone]_1_alpha_subcomplex_subunit_12_OS = Homo_sapiens_GN = NDUFA12_PE = 1_SV = 1 | 3.951 |
| >ENSG00000184831_sp_Q9BUR5_MIC26_HUMAN_MICOS_complex_subunit_MIC26_OS = Homo_sapiens_GN = APOO_PE = 1_SV = 1 | 1.295 |
| >ENSG00000184983_sp_P56556_NDUA6_HUMAN_NADH_dehydrogenase_[ubiquinone]_1_alpha_subcomplex_subunit_6_OS = Homo_sapiens_GN = NDUFA6_PE = 1_SV = 3 | 7.352 |
| >ENSG00000186010_sp_Q9P0J0_NDUAD_HUMAN_NADH_dehydrogenase_[ubiquinone]_1_alpha_subcomplex_subunit_13_OS = Homo_sapiens_GN = NDUFA13_PE = 1_SV = 3 | 9.576 |
| >ENSG00000189043_sp_O00483_NDUA4_HUMAN_Cytochrome_c_oxidase_subunit_NDUFA4_OS = Homo_sapiens_GN = NDUFA4_PE = 1_SV = 1 | 16.41 |
| >ENSG00000198125_sp_P02144_MYG_HUMAN_Myoglobin_OS = Homo_sapiens_GN = MB_PE = 1_SV = 2 | 419.002 |
| >ENSG00000198336_sp_P12829_MYL4_HUMAN_Myosin_light_chain_4_OS = Homo_sapiens_GN = MYL4_PE = 1_SV = 3 | 3.588 |
| >ENSG00000198523_sp_P26678_PPLA_HUMAN_Cardiac_phospholamban_OS = Homo_sapiens_GN = PLN_PE = 1_SV = 1 | 6.387 |
| >ENSG00000203667_sp_Q5RI15_COX20_HUMAN_Cytochrome_c_oxidase_protein_20_homolog_OS = Homo_sapiens_GN = COX20_PE = 1_SV = 2 | 0.818 |
| >ENSG00000214253_sp_Q9Y3D6_FIS1_HUMAN_Mitochondrial_fission_1_protein_OS = Homo_sapiens_GN = FIS1_PE = 1_SV = 2 | 1.289 |
| >ENSG00000228253_sp_P03928_ATP8_HUMAN_ATP_synthase_protein_8_OS = Homo_sapiens_GN = MT-ATP8_PE = 1_SV = 1 | 1.782 |

FIG. 19 shows the results obtained using a leave one out cross validation (LOOCV, R2: 0.87, RMSE: 20.22). In FIG. 19, values were multiplied by 10000. Therefore, the method according to the invention is also adapted for predicting protein expression level values of different proteins in heart cell.

The protein sequences were encoded using the percentage of exposed residues (Janin et al., 1978 Conformation of amino acid side-chains in proteins. Journal of molecular biology, 125(3), 357-386).

Figure 20:
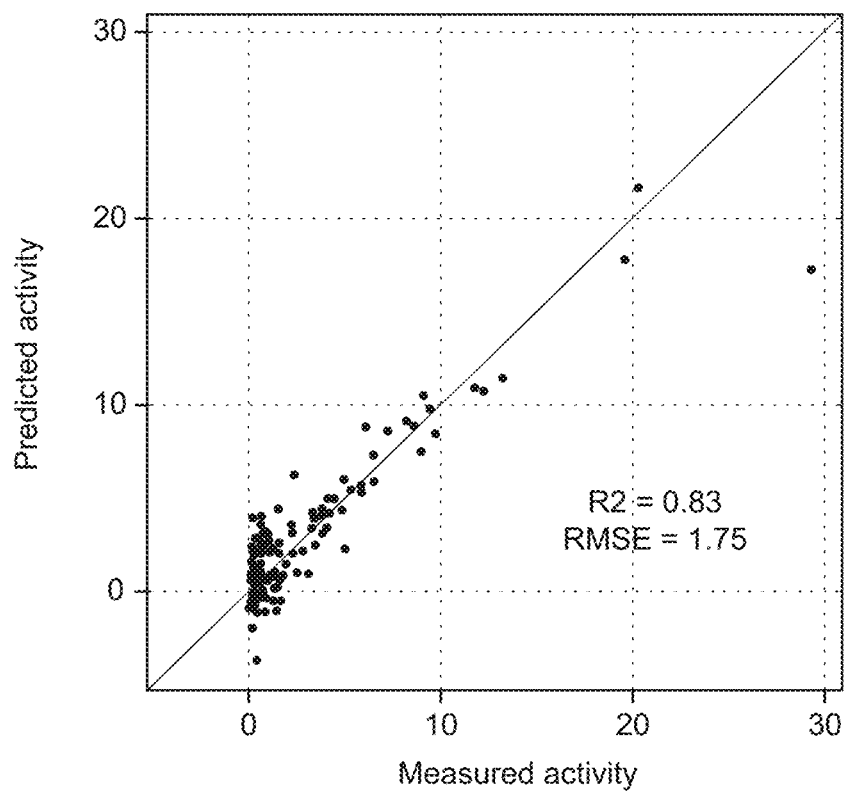
FIG. 20 is a view similar to that of FIG. 4 with predicted and measured values of protein expression levels for proteins in Kidney cell.

Example 11: Prediction of Protein Expression Level of Different Proteins in Kidney Cell (FIG. 20)

In this example, the method according to the invention was also used to predict protein expression level values of different proteins in Kidney cell. Proteins differ by amino acids composition and length. The data set (sequences and protein expression levels) are provided in Table 18 below.

TABLE 18 kidney proteins (as available from Uniprot) and protein expression

| KIDNEY PROTEIN | PROTEIN EXPRESSION |
|---|---|
| >ENSG00000005022_sp_P05141_ADT2_HUMAN_ADP/ATP_translocase_2_OS = Homo_sapiens_GN = SLC25A5_PE = 1_SV = 7 | 19.604 |
| >ENSG00000005187_sp_Q53FZ2_ACSM3_HUMAN_Acyl-coenzyme_A_synthetase_ACSM3,_mitochondrial_OS = Homo_sapiens_GN = ACSM3_PE = 1_SV = 2 | 0.497 |
| >ENSG00000005882_sp_Q15119_PDK2_HUMAN_[Pyruvate_dehydrogenase_(acetyl-transferring)]_kinase_isozyme_2,_mitochondrial_OS = Homo_sapiens_GN = PDK2_PE = 1_SV = 2 | 0.358 |
| >ENSG00000010932_sp_Q01740_FMO1_HUMAN_Dimethylaniline_monooxygenase_[N-oxide-forming]_1_OS = Homo_sapiens_GN = FMO1_PE = 2_SV = 3 | 0.695 |
| >ENSG00000014919_sp_Q7KZN9_COX15_HUMAN_Cytochrome_c_oxidase_assembly_protein_COX15_homolog_OS = Homo_sapiens_GN = COX15_PE = 1_SV = 1 | 0.249 |
| >ENSG00000016391_sp_Q8NE62_CHDH_HUMAN_Choline_dehydrogenase,_mitochondrial_OS = Homo_sapiens_GN = CHDH_PE = 1_SV = 2 | 1.576 |
| >ENSG00000050393_sp_Q96AQ8_MCUR1_HUMAN_Mitochondrial_calcium_uniporter_regulator_1_OS = Homo_sapiens_GN = MCUR1_PE = 1_SV = 1 | 0.261 |
| >ENSG00000055950_sp_Q8N983_RM43_HUMAN_39S_ribosomal_protein_L43,_mitochondrial_OS = Homo_sapiens_GN = MRPL43_PE = 1_SV = 1 | 0.526 |
| >ENSG00000060971_sp_P09110_THIK_HUMAN_3-ketoacyl-CoA_thiolase,_peroxisomal_OS = Homo_sapiens_GN = ACAA1_PE = 1_SV = 2 | 3.316 |
| >ENSG00000063241_sp_Q96AB3_ISOC2_HUMAN_Isochorismatase_domain-containing_protein_2_OS = Homo_sapiens_GN = ISOC2_PE = 1_SV = 1 | 1.595 |
| >ENSG00000072080_sp_Q13103_SPP24_HUMAN_Secreted_phosphoprotein_24_OS = Homo_sapiens_GN = SPP2_PE = 1_SV = 1 | 0.501 |
| >ENSG00000074410_sp_O43570_CAH12_HUMAN_Carbonic_anhydrase_12_OS = Homo_sapiens_GN = CA12_PE = 1_SV = 1 | 0.468 |
| >ENSG00000082515_sp_Q9NWU5_RM22_HUMAN_39S_ribosomal_protein_L22,_mitochondrial_OS = Homo_sapiens_GN = MRPL22_PE = 1_SV = 1 | 0.369 |
| >ENSG00000083750_sp_Q5VZM2_RRAGB_HUMAN_Ras-related_GTP-binding_protein_B_OS = Homo_sapiens_GN = RRAGB_PE = 1_SV = 1 | 0.375 |
| >ENSG00000089050_sp_O75884_RBBP9_HUMAN_Putative_hydrolase_RBBP9_OS = Homo_sapiens_GN = RBBP9_PE = 1_SV = 2 | 0.594 |
| >ENSG00000095932_sp_O75264_SIM24_HUMAN_Small_integral_membrane_protein_24_OS = Homo_sapiens_GN = SMIM24_PE = 2_SV = 2 | 0.804 |
| >ENSG00000100031_sp_P19440_GGT1_HUMAN_Gamma-glutamyltranspeptidase_1_OS = Homo_sapiens_GN = GGT1_PE = 1_SV = 2 | 4.148 |
| >ENSG00000100253_sp_Q9UGB7_MIOX_HUMAN_Inositol_oxygenase_OS = Homo_sapiens_GN = MIOX_PE = 1_SV = 1 | 0.566 |
| >ENSG00000100294_sp_Q8IVS2_FABD_HUMAN_Malonyl-CoA-acyl_carrier_protein_transacylase,_mitochondrial_OS = Homo_sapiens_GN = MCAT_PE = 1_SV = 2 | 0.181 |
| >ENSG00000102967_sp_Q02127_PYRD_HUMAN_Dihydroorotate_dehydrogenase_(quinone),_mitochondrial_OS = Homo_sapiens_GN = DHODH_PE = 1_SV = 3 | 0.347 |
| >ENSG00000103266_sp_Q9UNE7_CHIP_HUMAN_E3_ubiquitin-protein_ligase_CHIP_OS = Homo_sapiens_GN = STUB1_PE = 1_SV = 2 | 0.641 |
| >ENSG00000103485_sp_Q15274_NADC_HUMAN_Nicotinate-nucleotide_pyrophosphorylase_[carboxylating]_OS = Homo_sapiens_GN = QPRT_PE = 1_SV = 3 | 4.437 |
| >ENSG00000104324_sp_Q9Y646_CBPQ_HUMAN_Carboxypeptidase_Q_OS = Homo_sapiens_GN = CPQ_PE = 1_SV = 1 | 0.728 |
| >ENSG00000104327_sp_P05937_CALB1_HUMAN_Calbindin_OS = Homo_sapiens_GN = CALB1_PE = 1_SV = 2 | 3.860 |
| >ENSG00000105364_sp_Q9BYD3_RM04_HUMAN_39S_ribosomal_protein_L4,_mitochondrial_OS = Homo_sapiens_GN = MRPL4_PE = 1_SV = 1 | 0.370 |
| >ENSG00000108187_sp_P30039_PBLD_HUMAN_Phenazine_biosynthesis-like_domain-containing_protein_OS = Homo_sapiens_GN = PBLD_PE = 1_SV = 2 | 5.846 |
| >ENSG00000109062_sp_O14745_NHRF1_HUMAN_Na(+)/H(+)_exchange_regulatory_cofactor_NHE-RF1_OS = Homo_sapiens_GN = SLC9A3R1_PE = 1_SV = 4 | 5.314 |
| >ENSG00000109667_sp_Q9NRM0_GTR9_HUMAN_Solute_carrier_family_2,_facilitated_glucose_transporter_member_9_OS = Homo_sapiens_GN = SLC2A9_PE = 1_SV = 2 | 0.108 |
| >ENSG00000110013_sp_Q9HAT2_SIAE_HUMAN_Sialate_O-acetylesterase_OS = Homo_sapiens_GN = SIAE_PE = 1_SV = 1 | 1.100 |
| >ENSG00000112499_sp_O15244_S22A2_HUMAN_Solute_carrier_family_22_member_2_OS = Homo_sapiens_GN = SLC22A2_PE = 1_SV = 2 | 0.292 |
| >ENSG00000113492_sp_Q9BYV1_AGT2_HUMAN_Alanine--glyoxylate_aminotransferase_2,_mitochondrial_OS = Homo_sapiens_GN = AGXT2_PE = 1_SV = 1 | 1.382 |

TABLE 18-continued kidney proteins (as available from Uniprot) and protein expression

| KIDNEY PROTEIN | PROTEIN EXPRESSION |
|---|---|
| >ENSG00000114686_sp_P09001_RM03_HUMAN_39S_ribosomal_protein_L3,_mitochondrial_OS = Homo_sapiens_GN = MRPL3_PE = 1_SV = 1 | 0.511 |
| >ENSG00000115364_sp_P49406_RM19_HUMAN_39S_ribosomal_protein_L19,_mitochondrial_OS = Homo_sapiens_GN = MRPL19_PE = 1_SV = 2 | 0.369 |
| >ENSG00000116039_sp_P15313_VATB1_HUMAN_V-type_proton_ATPase_subunit_B,_kidney_isoform_OS = Homo_sapiens_GN = ATP6V1B1_PE = 1_SV = 3 | 0.413 |
| >ENSG00000116218_sp_Q9NP85_PODO_HUMAN_Podocin_OS = Homo_sapiens_GN = NPHS2_PE = 1_SV = 1 | 0.241 |
| >ENSG00000116771_sp_Q9BSE5_SPEB_HUMAN_Agmatinase,_mitochondrial_OS = Homo_sapiens_GN = AGMAT_PE = 1_SV = 2 | 9.447 |
| >ENSG00000116791_sp_Q08257_QOR_HUMAN_Quinone_oxidoreductase_OS = Homo_sapiens_GN = CRYZ_PE = 1_SV = 1 | 13.217 |
| >ENSG00000116882_sp_Q9NYQ3_HAOX2_HUMAN_Hydroxyacid_oxidase_2_OS = Homo_sapiens_GN = HAO2_PE = 1_SV = 1 | 0.575 |
| >ENSG00000117448_sp_P14550_AK1A1_HUMAN_Alcohol_dehydrogenase_[NADP(+)]_OS = Homo_sapiens_GN = AKR1A1_PE = 1_SV = 3 | 9.114 |
| >ENSG00000119414_sp_O00743_PPP6_HUMAN_Serine/threonine-protein_phosphatase_6_catalytic_subunit_OS = Homo_sapiens_GN = PPP6C_PE = 1_SV = 1 | 0.964 |
| >ENSG00000119655_sp_P61916_NPC2_HUMAN_Epididymal_secretory_protein_E1_OS = Homo_sapiens_GN = NPC2_PE = 1_SV = 1 | 4.853 |
| >ENSG00000119705_sp_Q9GZT3_SLIRP_HUMAN_SRA_stem-loop-interacting_RNA-binding_protein,_mitochondrial_OS = Homo_sapiens_GN = SLIRP_PE = 1_SV = 1 | 1.610 |
| >ENSG00000119979_sp_Q8TCE6_FA45A_HUMAN_Protein_FAM45A_OS = Homo_sapiens_GN = FAM45A_PE = 2_SV = 1 | 0.454 |
| >ENSG00000120509_sp_Q5EBL8_PDZ11_HUMAN_PDZ_domain-containing_protein_11_OS = Homo_sapiens_GN = PDZD11_PE = 1_SV = 2 | 0.261 |
| >ENSG00000123545_sp_Q9P032_NDUF4_HUMAN_NADH_dehydrogenase_[ubiquinone]_1_alpha_subcomplex_assembly_factor_4_OS = Homo_sapiens_GN = NDUFAF4_PE = 1_SV = 1 | 1.036 |
| >ENSG00000124299_sp_P12955_PEPD_HUMAN_Xaa-Pro_dipeptidase_OS = Homo_sapiens_GN = PEPD_PE = 1_SV = 3 | 2.299 |
| >ENSG00000124588_sp_P16083_NQO2_HUMAN_Ribosyldihydronicotinamide_dehydrogenase_[quinone]_OS = Homo_sapiens_GN = NQO2_PE = 1_SV = 5 | 2.442 |
| >ENSG00000124602_sp_Q8IV45_UN5CL_HUMAN_UNC5C-like_protein_OS = Homo_sapiens_GN = UNC5CL_PE = 1_SV = 2 | 0.113 |
| >ENSG00000125144_sp_P13640_MT1G_HUMAN_Metallothionein-1G_OS = Homo_sapiens_GN = MT1G_PE = 1_SV = 2 | 5.037 |
| >ENSG00000125434_sp_Q3KQZ1_S2535_HUMAN_Solute_carrier_family_25_member_35_OS = Homo_sapiens_GN = SLC25A35_PE = 2_SV = 1 | 0.190 |
| >ENSG00000126878_sp_Q9BQI0_AIF1L_HUMAN_Allograft_inflammatory_factor_1-like_OS = Homo_sapiens_GN = AIF1L_PE = 1_SV = 1 | 1.126 |
| >ENSG00000129151_sp_O75936_BODG_HUMAN_Gamma-butyrobetaine_dioxygenase_OS = Homo_sapiens_GN = BBOX1_PE = 1_SV = 1 | 3.795 |
| >ENSG00000129235_sp_Q9BRA2_TXD17_HUMAN_Thioredoxin_domain-containing_protein_17_OS = Homo_sapiens_GN = TXNDC17_PE = 1_SV = 1 | 1.535 |
| >ENSG00000132437_sp_P20711_DDC_HUMAN_Aromatic-L-amino-acid_decarboxylase_OS = Homo_sapiens_GN = DDC_PE = 1_SV = 2 | 3.364 |
| >ENSG00000132541_sp_P52758_UK114_HUMAN_Ribonuclease_UK114_OS = Homo_sapiens_GN = HRSP12_PE = 1_SV = 1 | 9.713 |
| >ENSG00000132744_sp_Q96HD9_ACY3_HUMAN_N-acyl-aromatic-L-amino_acid_amidohydrolase_(carboxylate-forming)_OS = Homo_sapiens_GN = ACY3_PE = 1_SV = 1 | 1.365 |
| >ENSG00000132840_sp_Q9H2M3_BHMT2_HUMAN_S-methylmethionine--homocysteine_S-methyltransferase_BHMT2_OS = Homo_sapiens_GN = BHMT2_PE = 1_SV = 1 | 1.752 |
| >ENSG00000133028_sp_O75880_SCO1_HUMAN_Protein_SCO1_homolog,_mitochondrial_OS = Homo_sapiens_GN = SCO1_PE = 1_SV = 1 | 1.025 |
| >ENSG00000133313_sp_Q96KP4_CNDP2_HUMAN_Cytosolic_non-specific_dipeptidase_OS = Homo_sapiens_GN = CNDP2_PE = 1_SV = 2 | 11.824 |
| >ENSG00000134864_sp_Q9BVM4_GGACT_HUMAN_Gamma-glutamylaminecyclotransferase_OS = Homo_sapiens_GN = GGACT_PE = 1_SV = 2 | 0.951 |
| >ENSG00000136463_sp_Q9BSH4_TACO1_HUMAN_Translational_activator_of_cytochrome_c_oxidase_1_OS = Homo_sapiens_GN = TACO1_PE = 1_SV = 1 | 0.810 |
| >ENSG00000137251_sp_Q9UJW2_TINAG_HUMAN_Tubulointerstitial_nephritis_antigen_OS = Homo_sapiens_GN = TINAG_PE = 2_SV = 3 | 3.407 |
| >ENSG00000137547_sp_Q9P015_RM15_HUMAN_39S_ribosomal_protein_L15,_mitochondrial_OS = Homo_sapiens_GN = MRPL15_PE = 1_SV = 1 | 0.677 |
| >ENSG00000137563_sp_Q92820_GGH_HUMAN_Gamma-glutamyl_hydrolase_OS = Homo_sapiens_GN = GGH_PE = 1_SV = 2 | 3.473 |
| >ENSG00000137673_sp_P09237_MMP7_HUMAN_Matrilysin_OS = Homo_sapiens_GN = MMP7_PE = 1_SV = 1 | 0.213 |
| >ENSG00000139194_sp_P82980_RET5_HUMAN_Retinol-binding_protein_5_OS = Homo_sapiens_GN = RBP5_PE = 1_SV = 3 | 4.240 |
| >ENSG00000139531_sp_P51687_SUOX_HUMAN_Sulfite_oxidase,_mitochondrial_OS = Homo_sapiens_GN = SUOX_PE = 1_SV = 2 | 1.800 |
| >ENSG00000140365_sp_Q9H0A8_COMD4_HUMAN_COMM_domain-containing_protein_4_OS = Homo_sapiens_GN = COMMD4_PE = 1_SV = 1 | 0.275 |
| >ENSG00000142910_sp_Q9GZM7_TINAL_HUMAN_Tubulointerstitial_nephritis_antigen-like_OS = Homo_sapiens_GN = TINAGL1_PE = 1_SV = 1 | 7.253 |

TABLE 18-continued kidney proteins (as available from Uniprot) and protein expression

| KIDNEY PROTEIN | PROTEIN EXPRESSION |
|---|---|
| >ENSG00000143436_sp_Q9BYD2_RM09_HUMAN_39S_ribosomal_protein_L9,_mitochondrial_OS = Homo_sapiens_GN = MRPL9_PE = 1_SV = 2 | 0.362 |
| >ENSG00000144035_sp_Q9UHE5_NAT8_HUMAN_N-acetyltransferase_8_OS = Homo_sapiens_GN = NAT8_PE = 1_SV = 2 | 2.828 |
| >ENSG00000145247_sp_Q56VL3_OCAD2_HUMAN_OCIA_domain-containing_protein_2_OS = Homo_sapiens_GN = OCIAD2_PE = 1_SV = 1 | 2.244 |
| >ENSG00000147614_sp_Q8N8Y2_VA0D2_HUMAN_V-type_proton_ATPase_subunit_d_2_OS = Homo_sapiens_GN = ATP6V0D2_PE = 2_SV = 1 | 0.101 |
| >ENSG00000148943_sp_Q9NUP9_LIN7C_HUMAN_Protein_lin-7_homolog_C_OS = Homo_sapiens_GN = LIN7C_PE = 1_SV = 1 | 0.887 |
| >ENSG00000149452_sp_Q8TCC7_S22A8_HUMAN_Solute_carrier_family_22_member_8_OS = Homo_sapiens_GN = SLC22A8_PE = 1_SV = 1 | 0.365 |
| >ENSG00000154025_sp_A0PJK1_SC5AA_HUMAN_Sodium/glucose_cotransporter_5_OS = Homo_sapiens_GN = SLC5A10_PE = 1_SV = 2 | 0.460 |
| >ENSG00000154814_sp_Q96HP4_OXND1_HUMAN_Oxidoreductase_NAD-binding_domain-containing_protein_1_OS = Homo_sapiens_GN = OXNAD1_PE = 1_SV = 1 | 0.144 |
| >ENSG00000156398_sp_Q96NB2_SFXN2_HUMAN_Sideroflexin-2_OS = Homo_sapiens_GN = SFXN2_PE = 1_SV = 2 | 2.540 |
| >ENSG00000157326_sp_Q9BTZ2_DHRS4_HUMAN_Dehydrogenase/reductase_SDR_family_member_4_OS = Homo_sapiens_GN = DHRS4_PE = 1_SV = 3 | 1.950 |
| >ENSG00000162366_sp_Q13113_PDZ1I_HUMAN_PDZK1-interacting_protein_1_OS = Homo_sapiens_GN = PDZK1IP1_PE = 1_SV = 1 | 1.328 |
| >ENSG00000162391_sp_Q8WW52_F151A_HUMAN_Protein_FAM151A_OS = Homo_sapiens_GN = FAM151A_PE = 2_SV = 2 | 0.446 |
| >ENSG00000162433_sp_P27144_KAD4_HUMAN_Adenylate_kinase_4,_mitochondrial_OS = Homo_sapiens_GN = AK4_PE = 1_SV = 1 | 8.643 |
| >ENSG00000162972_sp_Q8WWC4_CB047_HUMAN_Uncharacterized_protein_C2orf47,_mitochondrial_OS = Homo_sapiens_GN = C2orf47_PE = 1_SV = 1 | 0.597 |
| >ENSG00000163541_sp_P53597_SUCA_HUMAN_Succinyl-CoA_ligase_[ADP/GDP-forming]_subunit_alpha,_mitochondrial_OS = Homo_sapiens_GN = SUCLG1_PE = 1_SV = 4 | 8.211 |
| >ENSG00000164039_sp_Q9BUT1_BDH2_HUMAN_3-hydroxybutyrate_dehydrogenase_type_2_OS = Homo_sapiens_GN = BDH2_PE = 1_SV = 2 | 5.902 |
| >ENSG00000164237_sp_Q96DG6_CMBL_HUMAN_Carboxymethylenebutenolidase_homolog_OS = Homo_sapiens_GN = CMBL_PE = 1_SV = 1 | 12.223 |
| >ENSG00000164494_sp_Q86YH6_DLP1_HUMAN_Decaprenyl-diphosphate_synthase_subunit_2_OS = Homo_sapiens_GN = PDSS2_PE = 1_SV = 2 | 0.066 |
| >ENSG00000165644_sp_Q86VU5_CMTD1_HUMAN_Catechol_O-methyltransferase_domain-containing_protein_1_OS = Homo_sapiens_GN = COMTD1_PE = 1_SV = 1 | 0.290 |
| >ENSG00000165983_sp_Q96BW5_PTER_HUMAN_Phosphotriesterase-related_protein_OS = Homo_sapiens_GN = PTER_PE = 1_SV = 1 | 1.481 |
| >ENSG00000166126_sp_Q9BXJ7_AMNLS_HUMAN_Protein_amnionless_OS = Homo_sapiens_GN = AMN_PE = 1_SV = 2 | 0.746 |
| >ENSG00000166548_sp_O00142_KITM_HUMAN_Thymidine_kinase_2,_mitochondrial_OS = Homo_sapiens_GN = TK2_PE = 1_SV = 4 | 0.622 |
| >ENSG00000166840_sp_Q969I3_GLYL1_HUMAN_Glycine_N-acyltransferase-like_protein_1_OS = Homo_sapiens_GN = GLYATL1_PE = 1_SV = 1 | 1.064 |
| >ENSG00000168065_sp_Q9NSA0_S22AB_HUMAN_Solute_carrier_family_22_member_11_OS = Homo_sapiens_GN = SLC22A11_PE = 1_SV = 1 | 0.239 |
| >ENSG00000168672_sp_Q96KN1_FA84B_HUMAN_Protein_FAM84B_OS = Homo_sapiens_GN = FAM84B_PE = 1_SV = 1 | 0.199 |
| >ENSG00000169288_sp_Q9BYD6_RM01_HUMAN_39S_ribosomal_protein_L1,_mitochondrial_OS = Homo_sapiens_GN = MRPL1_PE = 1_SV = 2 | 0.711 |
| >ENSG00000169413_sp_Q93091_RNAS6_HUMAN_Ribonuclease_K6_OS = Homo_sapiens_GN = RNASE6_PE = 2_SV = 2 | 0.502 |
| >ENSG00000169504_sp_Q9Y696_CLIC4_HUMAN_Chloride_intracellular_channel_protein_4_OS = Homo_sapiens_GN = CLIC4_PE = 1_SV = 4 | 6.141 |
| >ENSG00000170482_sp_Q9UHI7_S23A1_HUMAN_Solute_carrier_family_23_member_1_OS = Homo_sapiens_GN = SLC23A1_PE = 1_SV = 3 | 0.252 |
| >ENSG00000171174_sp_Q9H477_RBSK_HUMAN_Ribokinase_OS = Homo_sapiens_GN = RBKS_PE = 1_SV = 1 | 0.643 |
| >ENSG00000172340_sp_Q96I99_SUCB2_HUMAN_Succinyl-CoA_ligase_[GDP-forming]_subunit_beta,_mitochondrial_OS = Homo_sapiens_GN = SUCLG2_PE = 1_SV = 2 | 4.961 |
| >ENSG00000174547_sp_Q9Y3B7_RM11_HUMAN_39S_ribosomal_protein_L11,_mitochondrial_OS = Homo_sapiens_GN = MRPL11_PE = 1_SV = 1 | 0.332 |
| >ENSG00000174827_sp_Q5T2W1_NHRF3_HUMAN_Na(+)/H(+)_exchange_regulatory_cofactor_NHE-RF3_OS = Homo_sapiens_GN = PDZK1_PE = 1_SV = 2 | 2.309 |
| >ENSG00000175287_sp_Q5SRE7_PHYD1_HUMAN_Phytanoyl-CoA_dioxygenase_domain-containing_protein_1_OS = Homo_sapiens_GN = PHYHD1_PE = 1_SV = 2 | 0.721 |
| >ENSG00000175581_sp_Q96GC5_RM48_HUMAN_39S_ribosomal_protein_L48,_mitochondrial_OS = Homo_sapiens_GN = MRPL48_PE = 1_SV = 2 | 0.272 |
| >ENSG00000175600_sp_Q9HAC7_SUCHY_HUMAN_Succinate--hydroxymethylglutarate_CoA-transferase_OS = Homo_sapiens_GN = SUGCT_PE = 1_SV = 2 | 0.347 |
| >ENSG00000175806_sp_Q9UJ68_MSRA_HUMAN_Mitochondrial_peptide_methionine_sulfoxide_reductase_OS = Homo_sapiens_GN = MSRA_PE = 1_SV = 1 | 1.247 |
| >ENSG00000176387_sp_P80365_DHI2_HUMAN_Corticosteroid_11-beta-dehydrogenase_isozyme_2_OS = Homo_sapiens_GN = HSD11B2_PE = 1_SV = 2 | 3.084 |

TABLE 18-continued kidney proteins (as available from Uniprot) and protein expression

| KIDNEY PROTEIN | PROTEIN EXPRESSION |
|---|---|
| >ENSG00000176946_sp_Q8WY91_THAP4_HUMAN_THAP_domain-containing_protein_4_OS = Homo_sapiens_GN = THAP4_PE = 1_SV = 2 | 0.202 |
| >ENSG00000177034_sp_Q5HYI7_MTX3_HUMAN_Metaxin-3_OS = Homo_sapiens_GN = MTX3_PE = 1_SV = 2 | 0.336 |
| >ENSG00000180185_sp_Q6P587_FAHD1_HUMAN_Acylpyruvase_FAHD1,_mitochondrial_OS = Homo_sapiens_GN = FAHD1_PE = 1_SV = 2 | 1.264 |
| >ENSG00000181035_sp_Q86VD7_S2542_HUMAN_Mitochondrial_coenzyme_A_transporter_SLC25A42_OS = Homo_sapiens_GN = SLC25A42_PE = 2_SV = 2 | 0.254 |
| >ENSG00000181610_sp_Q9Y3D9_RT23_HUMAN_28S_ribosomal_protein_S23,_mitochondrial_OS = Homo_sapiens_GN = MRPS23_PE = 1_SV = 2 | 0.565 |
| >ENSG00000182551_sp_Q9BV57_MTND_HUMAN_1,2-dihydroxy-3-keto-5-methylthiopentene_dioxygenase_OS = Homo_sapiens_GN = ADI1_PE = 1_SV = 1 | 0.737 |
| >ENSG00000182919_sp_Q9H0W9_CK054_HUMAN_Ester_hydrolase_C11orf54_OS = Homo_sapiens_GN = C11orf54_PE = 1_SV = 1 | 8.962 |
| >ENSG00000186335_sp_Q495M3_S36A2_HUMAN_Proton-coupled_amino_acid_transporter_2_OS = Homo_sapiens_GN = SLC36A2_PE = 1_SV = 1 | 0.347 |
| >ENSG00000189143_sp_O14493_CLD4_HUMAN_Claudin-4_OS = Homo_sapiens_GN = CLDN4_PE = 1_SV = 1 | 0.454 |
| >ENSG00000189283_sp_P49789_FHIT_HUMAN_Bis(5'-adenosyl)-triphosphatase_OS = Homo_sapiens_GN = FHIT_PE = 1_SV = 3 | 0.641 |
| >ENSG00000197375_sp_O76082_S22A5_HUMAN_Solute_carrier_family_22_member_5_OS = Homo_sapiens_GN = SLC22A5_PE = 1_SV = 1 | 0.017 |
| >ENSG00000197728_sp_P62854_RS26_HUMAN_40S_ribosomal_protein_S26_OS = Homo_sapiens_GN = RPS26_PE = 1_SV = 3 | 3.809 |
| >ENSG00000197901_sp_Q4U2R8_S22A6_HUMAN_Solute_carrier_family_22_member_6_OS = Homo_sapiens_GN = SLC22A6_PE = 1_SV = 1 | 0.290 |
| >ENSG00000198130_sp_Q6NVY1_HIBCH_HUMAN_3-hydroxyisobutyryl-CoA_hydrolase,_mitochondrial_OS = Homo_sapiens_GN = HIBCH_PE = 1_SV = 2 | 6.550 |
| >ENSG00000198203_sp_O00338_ST1C2_HUMAN_Sulfotransferase_1C2_OS = Homo_sapiens_GN = SULT1C2_PE = 1_SV = 1 | 0.592 |
| >ENSG00000213934_sp_P69891_HBG1_HUMAN_Hemoglobin_subunit_gamma-1_OS = Homo_sapiens_GN = HBG1_PE = 1_SV = 2 | 6.483 |
| >ENSG00000214274_sp_P03950_ANGI_HUMAN_Angiogenin_OS = Homo_sapiens_GN = ANG_PE = 1_SV = 1 | 1.651 |
| >ENSG00000223609_sp_P02042_HBD_HUMAN_Hemoglobin_subunit_delta_OS = Homo_sapiens_GN = HBD_PE = 1_SV = 2 | 29.319 |
| >ENSG00000241119_sp_O60656_UD19_HUMAN_UDP-glucuronosyltransferase_1-9_OS = Homo_sapiens_GN = UGT1A9_PE = 1_SV = 1 | 4.079 |
| >ENSG00000242110_sp_Q9UHK6_AMACR_HUMAN_Alpha-methylacyl-CoA_racemase_OS = Homo_sapiens_GN = AMACR_PE = 1_SV = 2 | 0.616 |
| >ENSG00000243989_sp_Q03154_ACY1_HUMAN_Aminoacylase-1_OS = Homo_sapiens_GN = ACY1_PE = 1_SV = 1 | 20.283 |
| >ENSG00000250799_sp_Q9UF12_PROD2_HUMAN_Probable_proline_dehydrogenase_2_OS = Homo_sapiens_GN = PRODH2_PE = 2_SV = 1 | 1.558 |
| >ENSG00000261701_sp_P00739_HPTR_HUMAN_Haptoglobin-related_protein_OS = Homo_sapiens_GN = HPR_PE = 2_SV = 2 | 0.658 |

FIG. 20 shows the results obtained using a leave one out cross validation (LOOCV, R2: 0.83, RMSE: 1.75) for 130 protein sequences. Again, the method according to the invention is therefore adapted for predicting protein expression level values, in particular for different proteins in Kidney cell.

The protein sequences were encoded using the Relative preference value at Mid (Richardson-Richardson, 1988 Amino acid preferences for specific locations at the ends of alpha helices. Science, 240(4859), 1648-1652).

Thus, R2 and RMSE between the predicted values and the measured values of several fitness such as protein expression level or mRNA expression level that were obtained in the aforementioned examples show that the prediction system 20 and method according to the invention allow an efficient prediction of different fitness values of different proteins or protein variants also for protein expression level and mRNA expression level.

What is claimed is:

1. A method for selecting and synthesizing a variant of a protein having a desired fitness, the method comprising:

encoding an amino acid sequence of each of a plurality of variants of the protein to be evaluated for having the desired fitness into a numerical sequence according to an index of biochemical or physico-chemical property values in a protein database, wherein the protein database includes a plurality of indices of said property values for each amino acid in each of the plurality of variants to be evaluated such that the numerical sequence comprises a property value for each amino acid of the sequence of each of the plurality of variants to be evaluated, said plurality of indices comprising an index selected from the group consisting of D Normalized frequency of extended structure, D Electron-ion interaction potential values, D SD of amino acid composition of total proteins, D pK-C and D Weights from the interfacial hydrophobicity (IFH) scale calculating a protein spectrum according to the numerical sequence for each of said plurality of variants to be evaluated by applying a Fourier transform to the numerical sequence such that each protein spectrum verifies the following equation:

$$|f_j| = \left| \sum_{k=0}^{N-1} x_k \exp\left(\frac{-2i\pi}{N} jk\right) \right|$$

where j is an index-number of the protein spectrum $|f_j|$; the numerical sequence includes N value(s) denoted $x_k$, with $0 \leq k \leq N-1$ and $N \geq 1$; and
i defining the imaginary number such that $i^2 = -1$;

determining a protein spectra database according to learning data comprising a plurality of protein spectrum values for each of a plurality of pre-existing variants other than the variants to be evaluated that have been experimentally tested in a wet lab for their biochemical or physico-chemical property values, such that each of said protein spectrum values of said pre-existing variants corresponds to a value of protein fitness comparing the calculated protein spectrum for each variant to be evaluated with protein spectrum values of the predetermined database;

predicting a value of said fitness according to the comparison step for each of said variants to be evaluated by determining the protein spectrum value in the protein spectra database that is the closest to the protein spectrum of each variant to be evaluated;

selecting the variant of the protein from the plurality of variants to be evaluated that has the predicted value of said fitness closest to the desired fitness value; and synthesizing the selected variant of the protein.

2. The method according to claim 1, wherein the calculated protein spectrum includes at least one frequency value and the calculated protein spectrum is compared with said protein spectrum values for each frequency value.

3. The method according to claim 1, wherein, during the encoding step, the protein database includes several indexes of property values; and wherein the method further includes a step of:

selecting the best index based on a comparison of measured fitness values for sample proteins with predicted fitness values previously obtained for said sample proteins according to each index;

the encoding step being then performed using the selected index.

4. The method according to claim 3, wherein, during the selection step, the selected index is the index with the smallest root mean square error, wherein the root mean square error for each index verifies the following equation:

$$RMSE_{Index\_j} = \sqrt{\sum_{i=1}^{S} \frac{(y_i - \hat{y}_{i,j})^2}{S}}$$

where $y_i$ is the measured fitness of the $i^{th}$ sample protein, $\hat{y}_{i,j}$ is the predicted fitness of the $i^{th}$ sample protein with the $j^{th}$ index, and
S the number of sample proteins.

5. The method according to claim 3, wherein, during the selection step, the selected index is the index with the coefficient of determination nearest to 1, wherein the coefficient of determination for each index verifies the following equation:

$$R^2_{Index\_j} = \frac{\left(\sum_{i=1}^{S} (y_i - \bar{y})(\hat{y}_{i,j} - \bar{\hat{y}})\right)^2}{\sum_{i=1}^{S} (y_i - \bar{y})^2 \sum_{i=1}^{S} (\hat{y}_{i,j} - \bar{\hat{y}})^2}$$

where $y_i$ is the measured fitness of the $i^{th}$ sample protein, $\hat{y}_{i,j}$ is the predicted fitness of the $i^{th}$ sample protein with the $j^{th}$ index,
S the number of sample proteins,
$\bar{y}$ is an average of the measured fitness for the S sample proteins, and
$\bar{\hat{y}}$ is an average of the predicted fitness for the S sample proteins.

6. The method according to claim 1, wherein the method further includes, after the encoding step and before the protein spectrum calculation step, the following step:

normalizing the numerical sequence obtained via the encoding step, by subtracting to each value of the numerical sequence a mean of the numerical sequence values;

the protein spectrum calculation step being then performed on the normalized numerical sequence.

7. The method according to claim 1, wherein the method further includes, after the encoding step and before the protein spectrum calculation step, the following step:

zero padding the numerical sequence obtained via the encoding step, by adding M zeros at one end of said numerical sequence, with M equal to (N−P) where N is a predetermined integer and P is the number of values in said numerical sequence;

the protein spectrum calculation step being then performed on the numerical sequence obtained further to the zero padding step.

8. The method according to claim 1, wherein the comparison step comprises determining, in the predetermined database of protein spectrum values for different values of said fitness, the protein spectrum value which is the closest to the calculated protein spectrum according to a predetermined criterion, the predicted value of said fitness being then equal to the fitness value which is associated in said database with the determined protein spectrum value.

9. The method according to claim 1, wherein, during the protein spectrum calculation step, several protein spectra are calculated for said protein according to several frequency ranges, and wherein, during the prediction step, an intermediate value of the fitness is estimated for each protein spectrum according to the comparison step, and the predicted value of the fitness is then computed using the intermediate fitness values.

10. The method according to claim 1, wherein the method includes a step of:

analysis of the protein according to the calculated protein spectrum, for screening of mutants libraries.

11. The method of claim 1, further comprising testing the selected variant that is synthesized in a wet laboratory to confirm the desired fitness.

12. The method of claim 10, wherein the analysis comprises analyzing each protein in a wet lab library of mutants comprising a plurality of mutant proteins according to the calculated protein spectrum.

13. The method of claim 1, further comprising testing the selected variant in a wet lab to obtain an actual value of said fitness of said selected variant to confirm the fitness of the selected variant.

14. A method for selecting and synthesizing a variant of a protein having a desired fitness, the method comprising:

encoding an amino acid sequence of each of a plurality of variants of the protein to be evaluated for having the desired fitness into a numerical sequence according to the selected index of biochemical or physico-chemical property values in a protein database, wherein the protein database includes a plurality of indices of said property values for each amino acid in each of the plurality of variants to be evaluated such that the numerical sequence comprises a property value for each amino acid of the sequence of each of the plurality of variants to be evaluated, said plurality of indices comprising an index selected from the group consisting of D Normalized frequency of extended structure, D Electron-ion interaction potential values, D SD of amino acid composition of total proteins, D pK-C and D Weights from the interfacial hydrophobicity (IFH) scale;

selecting the best index based on a comparison of measured fitness values for sample proteins with predicted fitness values previously obtained for said sample proteins according to each index;

calculating a protein spectrum according to the numerical sequence for each of said plurality of variants to be evaluated by applying a Fourier transform to the numerical sequence such that each protein spectrum verifies the following equation:

$$|f_j| = \left| \sum_{k=0}^{N-1} x_k \exp\left(\frac{-2i\pi}{N} jk\right) \right|$$

where j is an index-number of the protein spectrum $|f_j|$;
the numerical sequence includes N value(s) denoted $x_k$, with $0 \leq k \leq N-1$ and $N \geq 1$; and
i defining the imaginary number such that $i^2 = -1$;

determining a protein spectra database according to learning data comprising a plurality of protein spectrum values for each of a plurality of pre-existing variants other than the variants to be evaluated that have been experimentally tested in a wet lab for their biochemical or physico-chemical property values, such that each of said protein spectrum values of said pre-existing variants corresponds to a value of protein fitness comparing the calculated protein spectrum for each variant to be evaluated with protein spectrum values of the predetermined database;

predicting a value of said fitness according to the comparison step for each of said variants to be evaluated by determining the protein spectrum value in the protein spectra database that is the closest to the protein spectrum of each variant to be evaluated;

selecting the variant of the protein from the plurality of variants to be evaluated that has the predicted value of said fitness closest to the desired fitness value; and synthesizing the selected variant of the protein.

* * * * *